US008008258B2

(12) United States Patent
Aharoni et al.

(10) Patent No.: US 8,008,258 B2
(45) Date of Patent: Aug. 30, 2011

(54) COP 1 FOR TREATMENT OF INFLAMMATORY BOWEL DISEASES

(75) Inventors: Rina Aharoni, Rehovot (IL); Ruth Arnon, Rehovot (IL); Basak Kayhan, Ankara (TR)

(73) Assignee: Yeda Research and Development Co. Ltd., Rehovot (IL)

( * ) Notice: Subject to any disclaimer, the term of this patent is extended or adjusted under 35 U.S.C. 154(b) by 415 days.

(21) Appl. No.: 10/543,764

(22) PCT Filed: Jan. 20, 2004

(86) PCT No.: PCT/IL2004/000054
§ 371 (c)(1),
(2), (4) Date: May 1, 2006

(87) PCT Pub. No.: WO2004/064717
PCT Pub. Date: Aug. 5, 2004

(65) Prior Publication Data
US 2006/0264354 A1     Nov. 23, 2006

Related U.S. Application Data

(60) Provisional application No. 60/441,136, filed on Jan. 21, 2003.

(51) Int. Cl.
*A61K 38/02*     (2006.01)
(52) U.S. Cl. .......................... 514/13.2; 530/350; 514/1.1
(58) Field of Classification Search ........................ None
See application file for complete search history.

(56) References Cited

U.S. PATENT DOCUMENTS

| | | | | |
|---|---|---|---|---|
| 5,800,808 | A * | 9/1998 | Konfino et al. | 424/78.08 |
| 5,858,964 | A * | 1/1999 | Aharoni et al. | 514/2 |
| 5,981,589 | A * | 11/1999 | Konfino et al. | 514/561 |
| 6,048,898 | A * | 4/2000 | Konfino et al. | 514/561 |
| 6,054,430 | A * | 4/2000 | Konfino et al. | 514/12 |
| 6,214,791 | B1 * | 4/2001 | Arnon et al. | 514/2 |
| 6,342,476 | B1 * | 1/2002 | Konfino et al. | 514/2 |
| 6,362,161 | B1 * | 3/2002 | Konfino et al. | 514/2 |
| 6,620,847 | B2 * | 9/2003 | Konfino et al. | 514/561 |
| 6,939,539 | B2 * | 9/2005 | Konfino et al. | 424/78.08 |
| 7,199,098 | B2 * | 4/2007 | Konfino et al. | 514/2 |
| 2002/0055466 | A1 | 5/2002 | Aharoni et al. | |
| 2005/0171286 | A1 | 8/2005 | Konfino et al. | |
| 2006/0122113 | A1 | 6/2006 | Pinchasi et al. | |
| 2007/0021341 | A1 * | 1/2007 | Sela et al. | 514/12 |
| 2007/0117757 | A1 * | 5/2007 | Konfino et al. | 514/12 |

FOREIGN PATENT DOCUMENTS

| | | |
|---|---|---|
| WO | WO 00/05249 | 2/2000 |
| WO | WO 00/05250 * | 2/2000 |
| WO | 0018794 | 4/2000 |
| WO | WO 00/20010 * | 4/2000 |
| WO | WO 00/27417 * | 5/2000 |
| WO | WO 01/60392 A1 | 8/2001 |

OTHER PUBLICATIONS

Aharoni et al. "Copolymer 1 induces T cells of the T helper type 2 that crossreact with myelin basic protein and suppress experimental autoimmune encephalomyelitis" Proc. Natl. Acad. Sci., 1997, 94, 10821-6.*
Shanahan "Inflammatory Bowel Disease: Immunotherapeutics, Immunodiagnostics, and Ecotherapeutics" Gastroenterology, 2001, 120, 622-35.*
Rogler & Andus "Cytokines in Inflammatory Bowel Disease" World J. of Surg., 1998, 22, 382-9.*
Aharoni et al. "Bystander suppression of experimental autoimmune encephalomyelitis by T cell lines and clones of the Th2 type induced by copolymer 1" J. Neuroimmunology, 1998, 91, 135-46.*
Neuhaus et al. "Multiple sclerosis: Comparison of copolymer-1-reactive T cell lines from treated and untreated subjects reveals cytokine shift from T helper 1 to T helper 2 cells" Proc. Natl. Acad. Sci., 2000, 97, 7452-7.*
Swain "Blister packaging leads the way" Pharmaceutical and Medical Packaging News Magazine, 1999, pp. 1-4.*
FDA Label for COPAXONE (Copolymer-1) Jul. 12, 2001.*
U.S. Appl. No. 11/516,860, filed Sep. 6, 2006, Gad et al.
U.S. Appl. No. 11/528,894, filed Sep. 27, 2006, Aharoni et al.
U.S. Appl. No. 11/541,263, filed Sep. 29, 2006, Pinchasi et al.
U.S. Appl. No. 11/590,338, filed Oct. 30, 2006, Pinchasi et al.
Teitelbaum D., Copolymer 1 induces T cells of the T helper type 2 that crossreact with myelin basic protein and suppress experimental autoimmune encephalomyelitis, *Proc. Natl. Acad. Sci. U.S.A.,* Sep. 1997, 94(20), 10821-10826.
Sandborn W.J. (2005) "State-of-the-Art: Targeting Immunoregulation—Biologicals," *Inflammatory Bowel Disease Translation from Basic Research to Clinical Practice,* Falk Symposium 140, pp. 90-97.
Vandenbroucke K, et al. (2010) "Orally Administered *L. lactis* Secreting an Anti-TNF Nanobody Demonstrate Efficacy in Chronic Colitis," *Mucosal Immunol.* 3(1):pp. 49-56 (Abstract Only).
Ashizuka S, et al. (2009) "Adrenomedullin Treatment Reduces Intestinal Inflammation and Maintains Epithelial Barrier Function in Mice Administered Dextran Sulphate Sodium," *Microbol Immunol.* 53(10): pp. 573-581 (Abstract Only).
Chen G, et al. (2010) "Blockade of Complement Activation Product C5a Activity Using Specific Antibody Attenuates Intestinal Damage in Trinitrobenzene Sulfonic Acid Induced Model of Colitis," *Lab Invest.* [Epub ahead of print] (Abstract Only).
Nishitani Yosuke, (2009) "*Lactococcus lactic* Subsp. Cremoris FC Alleviates Symptoms of Colitis Induced by Dextran Sulfate Sodium in Mice," *International Immunopharmacology,* 9 : pp. 1444-1451.
Mileti Erika, et al. (2009) "Comparison of the Immunomodulatory Properties of Three Probiotic Strains of Lactobacilli Using Complex Culture Systems: Prediction for In Vivo Efficacy," *PLoS ONE* 4(9): e7056.

(Continued)

*Primary Examiner* — Christina Bradley
(74) *Attorney, Agent, or Firm* — John P. White; Cooper & Dunham LLP

(57) ABSTRACT

The present invention relates to the use of Copolymer 1 (glatiramer acetate), a Copolymer 1-related polypeptide, or a Copolymer 1-related peptide, for the treatment of inflammatory bowel diseases such as Crohn's disease and ulcerative colitis.

22 Claims, 13 Drawing Sheets

OTHER PUBLICATIONS

Bai Aiping, et al. (2010) "Novel Anti-Inflammatory Action of 5-Aminoimidazole-4-carboxamide Ribonucleoside with Protective Effect in Dextran Sulfate Sodium-Induced Acute and Chronic Colitis," *The Journal of Pharmocology and Experimental Therapeutics*, 333: pp. 717-725.

Bai Aiping, et al. (2009) "All-Trans Retinoic Acid Down-Regulates Inflammatory Responses by Shifting the Treg/Th17 Profile in Human Ulcerative and Murine Colitis," *Journal of Leukocyte Biology*, 86: pp. 959-969.

Srinivasan Mythily and Summerlin Don-Jon (2009), "Modulation of the Colonic Epithelial Cell Responses and Amelioration and Inflammation by CD80 Blockade in TNBS Colitis," *Clinical Immunology*, 133: pp. 411-421.

Bai Aiping, et al. (2010) "AMPK Agonist Downregulates Innate and Adaptive Immune Responses in TNBS-induced Murine," *Biochemical Pharmacology*, 80: pp. 1708-1717.

Danese S. and Angelucci E. (2009) "New and Emerging Biologics in the Treatment of Inflammatory Bowel Disease: Quo Vadis?" *Gastroenterol Clin Biol.*, 33 Suppl 3: pp. S217-S227.

Ng SC, et al. (2010) "Review Article: The Role of Non-Biological Drugs in Refractory Inflammatory Bowel Disease," *Aliment Pharmacol Ther.* [Epub ahead of print] (Abstract Only).

Buruiana FE, et al. (2010) "Recombinant Human Interleukin 10 for Induction of Remission in Crohn's Disease," *Cochrane Database Syst Rev.* 11:CD005109 (Abstract Only).

Yoshida Eric, M. (1999), "The Crohn's Disease Activity Index, Its Derivatives and the Inflammatory Bowel Disease Questionnaire: A Review of Instruments to Assess Crohn's Disease," *Can J Gastroenterol*, 13(1): pp. 65-73.

Ashizuka Shinya, et al. (2009), "Adrenomedullin Treatment Reduces Intestinal Inflammation and Maintains Epithelial Barrier Function in Mice Administered Dextran Sulphate Sodium," *Microbiol Immunol*, 53: pp. 573-581.

Billerey-Larmonier Claire (2008), "Protective Effects of Dietary Curcumin in Mouse Model of Chemically Induced Colitis Are Strain Dependent," *Inflamm Bowel Dis*, 14(6): pp. 780-793.

Buruiana FE, et al. (2010), "Recombinant Human Interleukin 10 for Induction of Remission in Crohn's Disease (Review)," *Cochrane Database of Systematic Review 2010*, 11: pp. 1-22.

Chen Guojiang, et al. (2010), "Blockade of Complement Activation Product C5a Activity Using Specific Antibody Attenuates Intestinal Damage in Trinitrobenzene Sulfonic Acid Induced Model of Colitis," *Laboratory Investigation*, pp. 1-12.

Danese S. and Angelucci E. (2009), "New and Emerging Biologics in the Treatment of Inflammatory Bowel Disease: Quo Vadis? Quelles Biotherapies pour Demain dans les Maladies Inflammatoires Chroniques Intestinales?" *Gastroenterologie Clinique et Biologique*, 33 (3) : pp. S217-S227.

Elson Charles, O., et al. (1995), "Experimental Models of Inflammatory Bowel Disease," *Gastroenterology*, 109: pp. 1344-1367.

Harvey R.F. and Bradshaw J.M. (1980), "A Simple Index of Crohn's-Disease Activity," *The Lancet*, p. 514.

Sostegni R., et al. (2003), "Review Article: Crohn's Disease: Monitoring Disease Activity," *Aliment Pharmacol Ther*, 17(2): pp. 11-17.

Neurath Markus, E., et al. (1995), "Antibodies to Interleukin 12 Abrogate Established Experimental Colitis in Mice," *The Journal of Experimental Medicine*, 182: pp. 1281-1290.

Ng S.C., et al. (2010), Review Article: The Role of Non-Biological Drugs in Refractory Inflammatory Bowel Disease, *Aliment Pharamcol Ther*, pp. 1-11.

Parkes M. and Jewell D.P. (2001), "Review Article: The Management of Severe Crohn's Disease," *Aliment Pharmacol Ther*, 15: pp. 563-573.

Strober Warren, et al. (2002), "The Immunology of Mucosal Models of Inflammation," *Annu. Rev. Immunol.*, 20: pp. 495-549.

Vandenbroucke K., et al. (2010), "Orally Administered *L. lactis* Secreting an Anti-TNF Nanobody Demonstrate Efficacy in Chronic Colitis," *Mucosal Immunology*, 3(1): pp. 49-56.

Macdonald T.T., et al. (2000), "Recent Development in the Immunology of Inflammatory Bowel Disease," *Scan. J. Immunol.*, 51: pp. 2-9.

Sandborn William and Targan Stephan (2002), "Biologic Therapy of Inflammatory Bowel Disease," *Gastroenterology*, 122: pp. 1592-1608.

Office Action issued Apr. 11, 2011 in connection with Canadian Patent Application No. 2,513,567.

Haupt et al., (2002) "Regional Peptide Uptake Study in the Rat Intestinal Mucosa: Glatiramer Acetate as a Model Drug," *Pharmaceutical Research*, 19(6):832-837.

\* cited by examiner

● Colitis   ○ GA Oral   ※ Ethanol Alone   × Normal

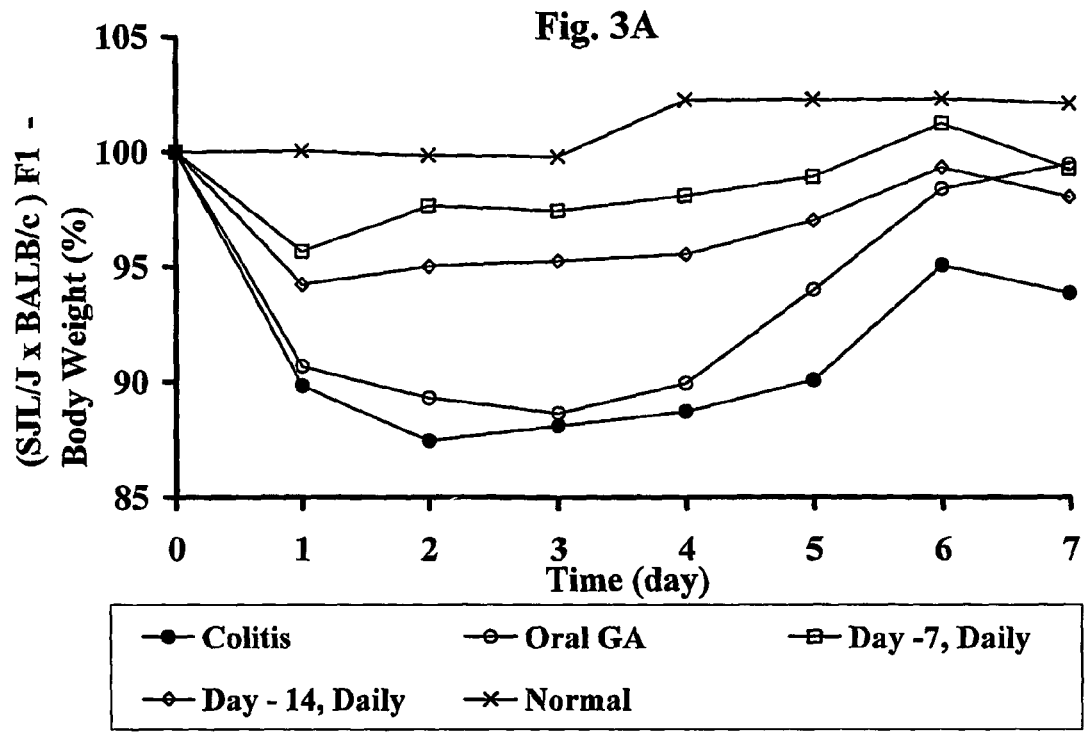
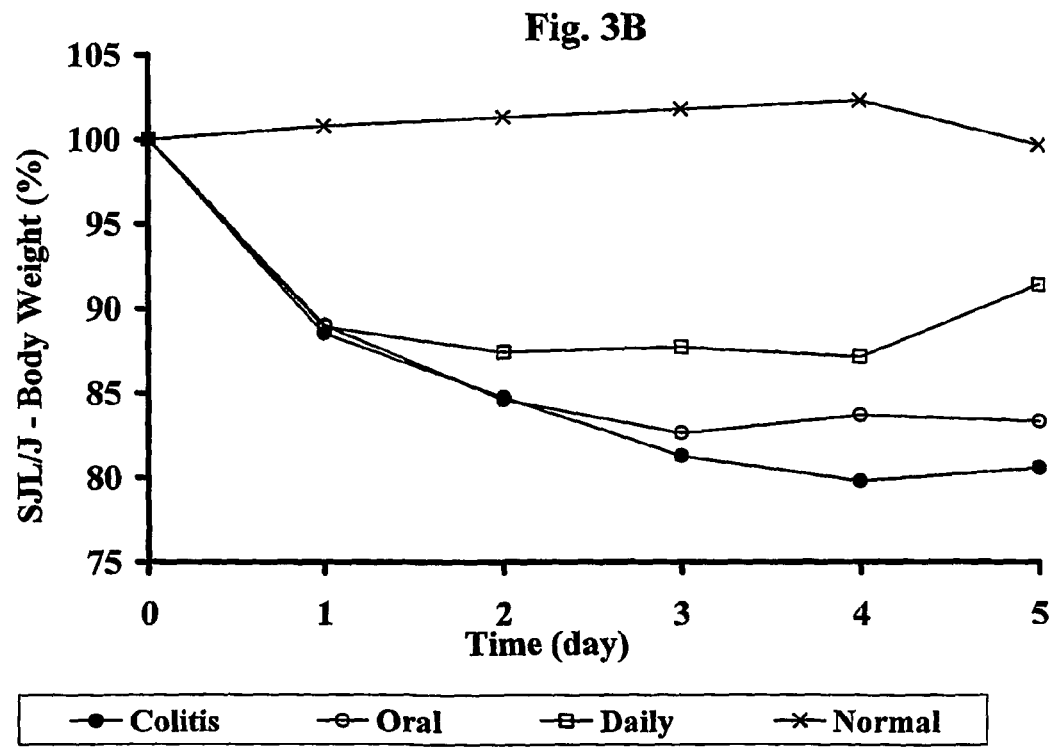

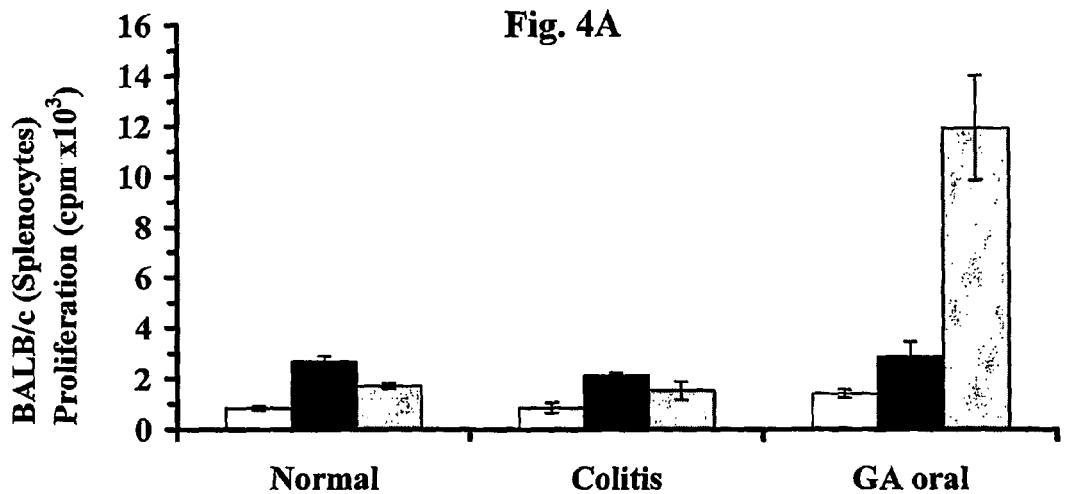
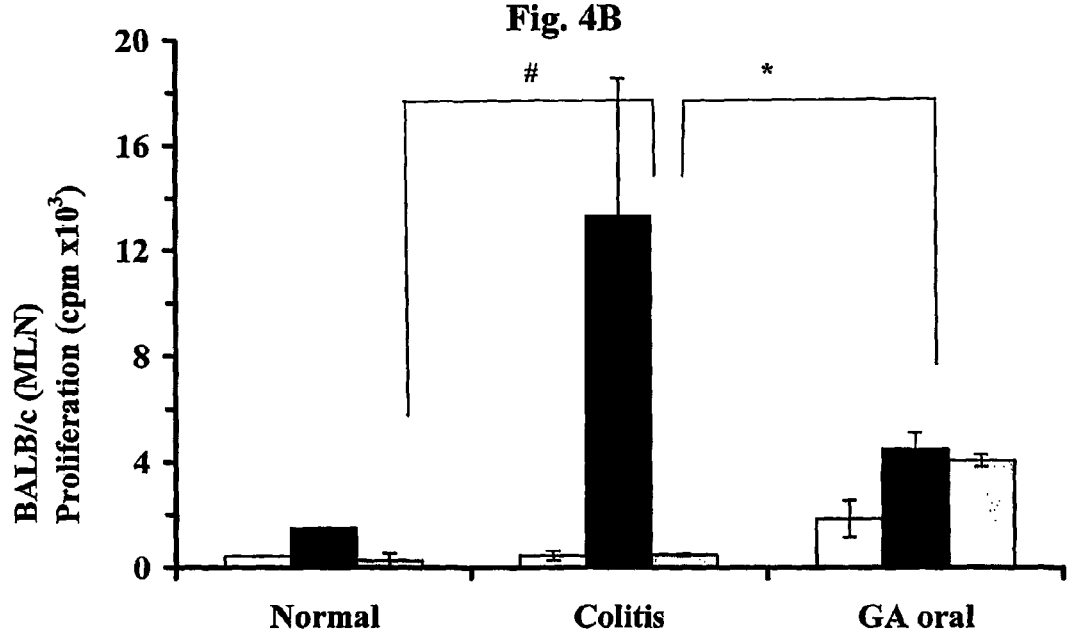

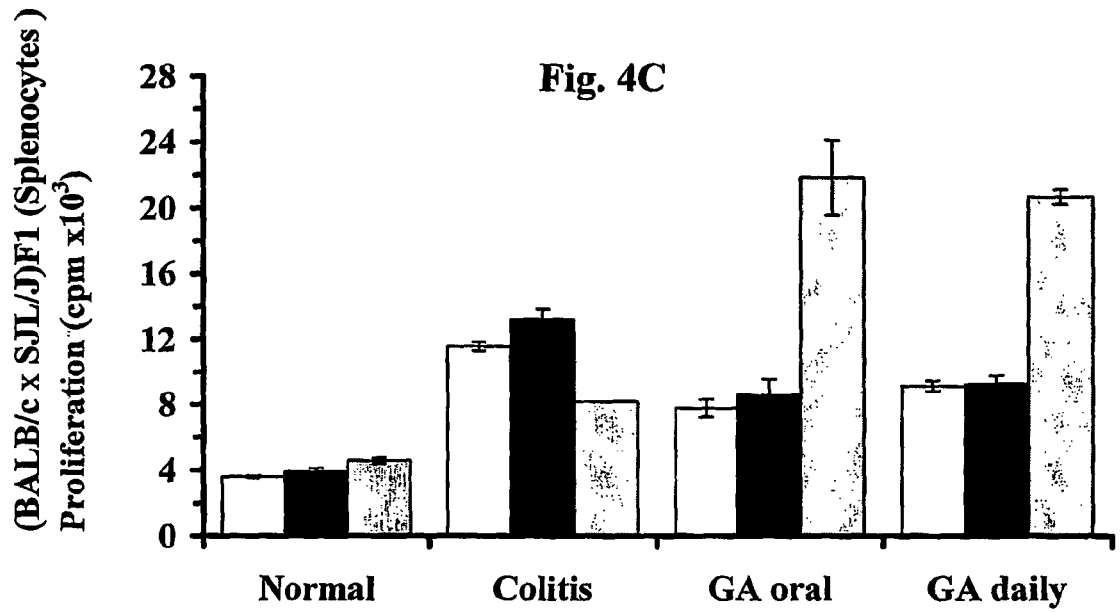
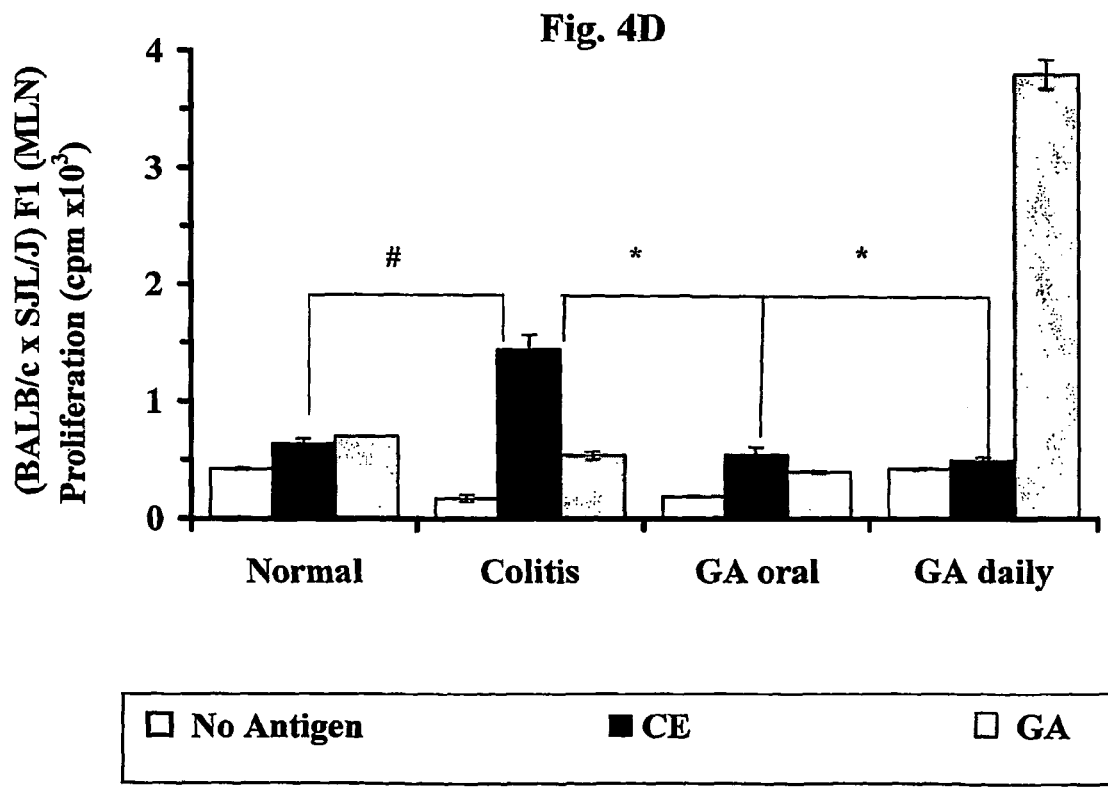

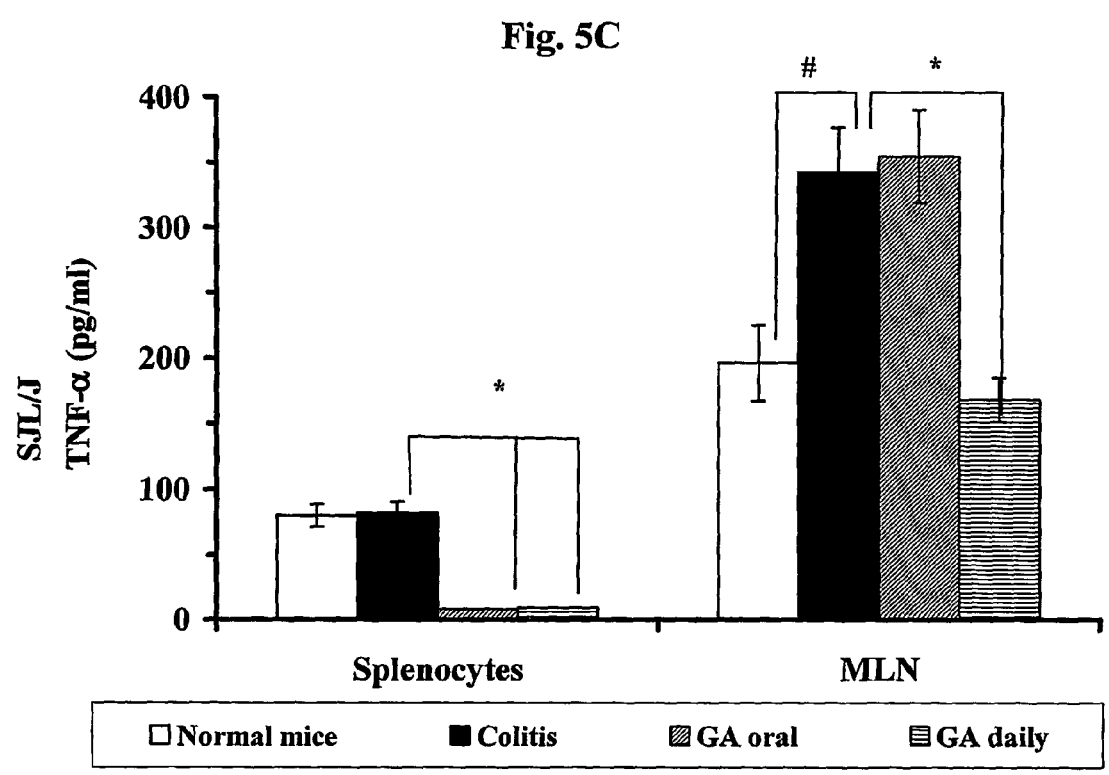

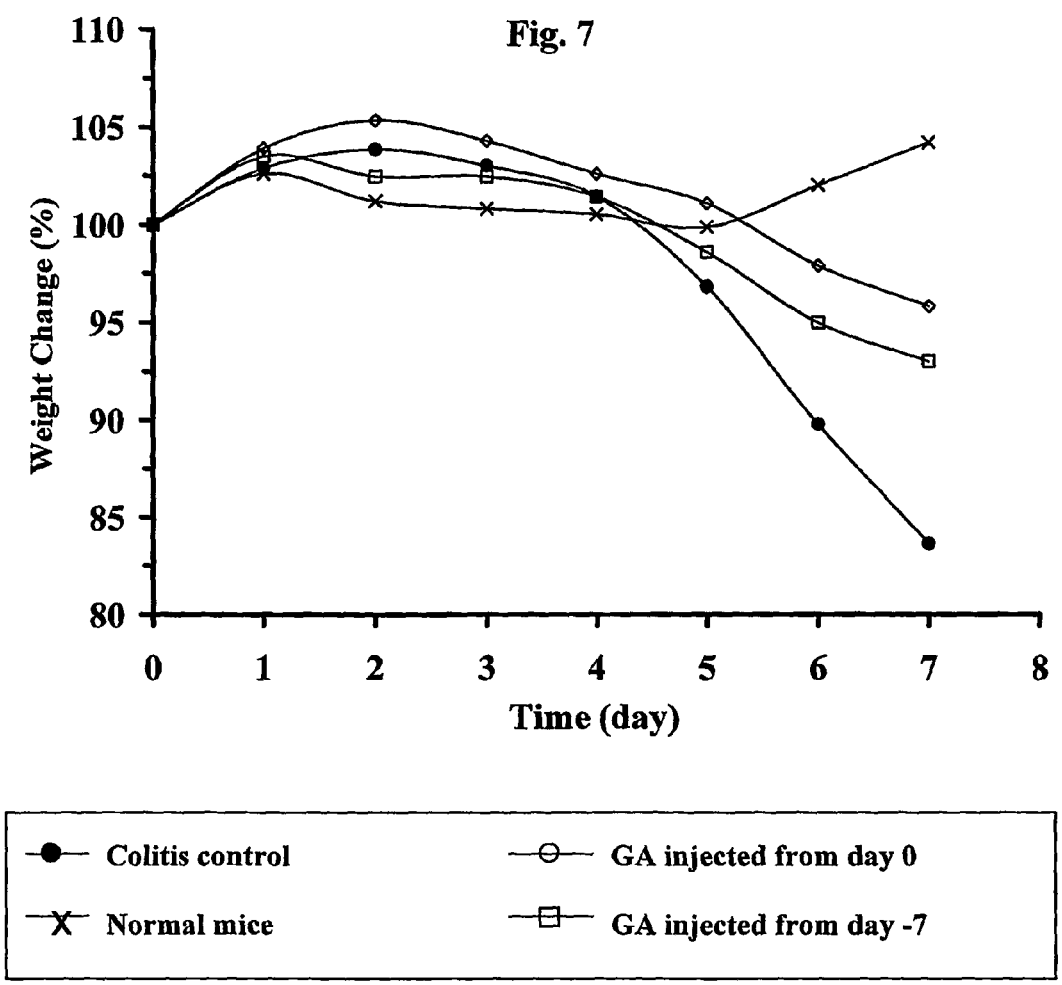

COP 1 FOR TREATMENT OF INFLAMMATORY BOWEL DISEASES

This application is a §371 National Stage of PCT International Application No. PCT/IL2004/000054, filed Jan. 20, 2004, claiming priority of U.S. Provisional Application No. 60/441,136, filed Jan. 21, 2003, the contents of which are hereby incorporated by reference.

FIELD OF THE INVENTION

The present invention relates to pharmaceutical compositions and methods for the treatment of inflammatory bowel diseases (IBD), particularly Crohn's disease and ulcerative colitis.

BACKGROUND OF THE INVENTION

Inflammatory bowel diseases (IBD) is the name given to a group of related diseases affecting the gastrointestinal tract, mainly Crohn's disease and ulcerative colitis, two severe gastrointestinal disorders of high frequency (more than one in 500 Americans has some type of inflammatory bowel disease) and disabling for many patients, and generating a significant burden on the health care system. Patients may have diarrhea, nauseas, vomiting, abdominal cramps, and pain that can be difficult to control. IBDs are characterized by chronic excessive destruction of the colon (in ulcerative colitis) or the small and large bowel (in Crohn's disease), due to the infiltration of the bowel wall by inflammatory infiltrate.

The pathogenesis of IBD involves interactions among local environment microorganisms, genetic susceptibility and the immune system. Several microorganisms, bacteria and viruses, have been implicated as etiologic agents of IBD, however, no evidence of a definite role for one infectious agent has been provided. Recent data suggest some susceptibility genes, yet extensive studies are still required to identify the specific genes responsible for the expression of such diseases. Whereas the nature of both possible infectious agents and genetic alteration remains unclear, great progress has been achieved in understanding the immune mechanisms responsible for the pathogenesis of IBD, particularly Crohn's disease.

CD4$^+$ Th1 cells have been identified as central mediators in the pathogenesis of Crohn's disease, showing restricted but variable TCR repertoire. IFN-$\gamma$ released by these Th1 cells activates local macrophages to produce pro-inflammatory cytokines and toxic metabolites, in particular TNF-$\alpha$ and nitric oxide (NO), which cause damage to the intestinal epithelium and maintain the transmural inflammation. This chronic abnormal Th1 response is maintained by the abrogation of tolerance to components of the intestinal flora or its products, resulting in an autoimmune-like process. Since a specific host autoantigen has not been identified, IBDs are not genuine autoimmune diseases. However, due to its immune nature, IBD may be viewed as such.

Copolymer 1 (Cop 1, glatiramer acetate or GA), a non-pathogenic synthetic random copolymer composed of the four amino acids: L-Glu, L-Lys, L-Ala, and L-Tyr (hereinafter "Cop 1" or "GA"), is currently an approved drug for the treatment of multiple sclerosis under the name of Copaxone™ (Sela and Teitelbaum, 2001). It is a very well tolerated agent with only minor adverse reactions and high safety profile. Treatment with Cop 1 by ingestion or inhalation is disclosed in U.S. Pat. No. 6,214,791.

Recently it was found that in animal models Cop 1 provides a beneficial effect for several additional disorders. Thus, Cop 1 suppresses the immune rejection manifested in graft versus host disease (GVHD) in case of bone marrow transplantation (Schlegel et al., 1996; U.S. Pat. No. 5,858,964), as well as in graft rejection in case of solid organ transplantation (Aharoni et al., 2001).

WO 01/52878 and WO 01/93893 disclose that Cop 1, Cop 1-related peptides and polypeptides and T cells activated therewith protect CNS cells from glutamate toxicity and prevent or inhibit neuronal degeneration or promote nerve regeneration in the central nervous system and peripheral nervous system. Thus, for example, Cop 1 is under evaluation as a therapeutic vaccine for neurodegenerative diseases such as optic neuropathies and glaucoma (Kipnis and Schwartz, 2002).

Cop 1 and related copolymers and peptides have been disclosed in WO 00/05250 (Aharoni et al., 2000), hereby incorporated by reference in its entirety as if fully disclosed herein, for treating autoimmune diseases. Although colitis is mentioned among the autoimmune diseases, no example or protocol for testing colitis is disclosed in said application.

The available medical treatments for IBD are rather unsatisfactory. A detrimental immune response towards local microorganisms, involving mainly CD4+ Th1 cells, and imbalance between pro-inflammatory and anti-inflammatory reactivity, play a role in the pathogenesis of IBD, particularly in Crohn's disease (CD) (MacDonald et al., 2000; Shanahan, 2001). Current medical treatments for IBD rely on the use of non-specific anti-inflammatory drugs such as corticosteroids, as well as immunosuppressive drugs (Shanahan, 2001). However, these treatments do not modify the disease course but only ameliorate the symptoms, while inducing severe side effects that limit their use. Moreover, significant percentage of the patients are steroid resistance. Hence, there is a real need for new, well-tolerated therapies that effectively induce remission and alter the natural course of the disease. Based on the immunopathological nature of CD, novel immunomodulatory strategies attempt to deviate the CD4+ pathogenic T-cells from Th1 inflammatory to Th2 anti-inflammatory phenotype (Shanahan, 2001; Sandborn and Targan, 2002; Van Deventer, 2000).

SUMMARY OF THE INVENTION

It has now been found, in accordance with the present invention, that treatment of 2,4,6-trinitrobenzenesulfonic acid (TNBS)-induced colitis mice with Cop 1 can protect the mice from the disease.

The present invention thus relates, in one aspect, to a method for treatment of a patient suffering from an inflammatory bowel disease (IBD), which comprises administering to said patient an effective amount of an active agent selected from the group consisting of Cop 1, a Cop 1-related polypeptide, and a Cop 1-related peptide. Among the effects obtained by this treatment are included, for example, reduction of disease progression, alleviation of the disease symptoms, suppression of the inflammatory process and/or prevention of further exacerbation of the disease.

The inflammatory bowel disease (IBD) to be treated according to the invention is any disease in which detrimental immune reactivity is manifested in the gut (intestine), particularly Crohn's disease and ulcerative colitis.

In another aspect, the present invention provides a pharmaceutical composition for treatment of an inflammatory bowel disease (IBD), particularly Crohn's disease and ulcerative colitis, comprising an active agent selected from the group consisting of Cop 1, a Cop 1-related polypeptide, and a Cop 1-related peptide, and optionally a pharmaceutically acceptable carrier.

In a further aspect, the present invention relates to the use of an active agent selected from the group consisting of Cop 1, a Cop 1-related polypeptide, and a Cop 1-related peptide, for the manufacture of a pharmaceutical composition for treatment of an inflammatory bowel disease (IBD), particularly Crohn's disease and ulcerative colitis.

In yet another aspect, the present invention provides an article of manufacture comprising packaging material and a pharmaceutical composition contained within the packaging material, said pharmaceutical composition comprising an agent selected from the group consisting of Copolymer 1, a Copolymer 1-related peptide, and a Copolymer 1-related polypeptide; and said packaging material includes a label that indicates that said agent is therapeutically effective for treating an inflammatory bowel disease.

BRIEF DESCRIPTION OF THE FIGURES

FIG. 1A is a photograph, showing macroscopic manifestations: gross appearance of representative colons, 7 days after TNBS inoculation, demonstrating: normal colon, colon of TNBS-induced colitis from untreated mouse (with ulceration at two sites, major adhesions, diarrhea and bowel thickness, graded 8); colons from two mice treated orally with Cop 1 (0.25 mg/mouse, 8 feedings) with only focal hyperemia (graded 1). FIG. 1B is a graph showing weight changes and FIG. 1C is a graph showing survival rates of BALB/c mice with TNBS-induced colitis and orally treated with GA as compared with untreated colitic mice and with normal mice or mice that were inoculated with 50% ethanol alone. The weights of GA-treated mice were significantly higher than those of untreated mice ($p<0.05$). Mice that died during the first 2 days were considered as treatment casualties and were not taken into consideration. Each group consisted of 5-7 mice that survived after 2 days. Results represent one of three similar experiments.

FIGS. 3A-3F show the effect of various GA treatments on TNBS-induced colitis in different mouse strains. Weight changes (FIGS. 3A, 3B); Survival rates (FIGS. 3C, 3D); Histological scores (FIGS. 3E, 3F). Disease was induced by rectal instillation of TNBS in 50% alcohol in (SJL/JxBALB/c)F1 mice (FIGS. 3A, 3C, 3E) or SJL/J mice (FIGS. 3B, 3D, 3F). Colitic untreated mice are compared with GA-treated mice by either oral treatment (250 µg/feeding, at alternate days, starting 7 days before disease induction) or by daily injections (2.5 mg/mouse subcutaneously (SC) in PBS, starting either 7 or 14 days before induction). The weights of GA-injected mice from both strains, were significantly higher than those of untreated mice ($p<0.05$). *Indicates statistical significance in histological manifestations ($p<0.05$). Each group consists of 7-11 mice that survived 2 days after disease induction.

FIGS. 4A-4F show the effect of GA on the lymphocyte proliferation in different mouse strains. The responses of normal mice, colitis-induced mice, and colitis-induced mice treated with GA orally or parenterally daily are compared in the BALB/c (FIGS. 4A, 4B), (SJL/JxBALB/c)F1 (FIGS. 4C, 4D), and SJL/J (FIGS. 4E, 4F) strains. Cells from spleens (FIGS. 4A, 4C, 4E) and mesenteric lymph nodes (MLN) (FIGS. 4B, 4D, 4F) were cultured, 7 days after disease induction, with no antigen, colonic extract (CE, 200 µg/ml), or GA (50 µg/ml). Results of thymidine incorporation are expressed as mean cpm±ISD of six culture wells and represent one of two similar experiments, using pooled cells from 3-5 mice in each group. # Indicates significant increase in the response to CE by colitic mice. * Indicates significant decrease in the response to CE induced by GA treatment.

FIGS. 5A-5C show the effect of GA on TNF-α secretion in different mouse strains. The responses of normal mice, colitis-induced mice, and colitis-induced mice treated with GA orally or parenterally daily are compared in the BALB/c (FIG. 5A), (SJL/JxBALB/c)F1 (FIG. 5B), and SJL/J (FIG. 5C) strains. Cells from spleens and mesenteric lymph nodes (MLN) were cultured, 7 days after disease induction, with immobilized anti-CD3 (5 µg/ml). After 24 hours, supernatants from six culture wells were pooled and TNF-α was measured by ELISA in duplicates. Results are expressed as TNF-α concentration (pg/ml±SD) and represent one of two similar experiments, using pooled cells from 3-5 mice in each group. # Indicates significant increase in TNF-α in colitic mice in comparison to normal mice. * Indicates significant decrease in TNF-α induced by GA treatment in comparison to untreated colitis induced mice.

FIG. 7 shows the effect of GA treatment on weight change of dextran sulfate sodium (DSS)-induced colitis in C57BL/6 mice. GA was administered subcutaneously by daily injections—2.5 mg/day, in PBS, starting either 7 days before, or in the same day of DSS feeding.

DETAILED DESCRIPTION OF THE INVENTION

Figure 1A:
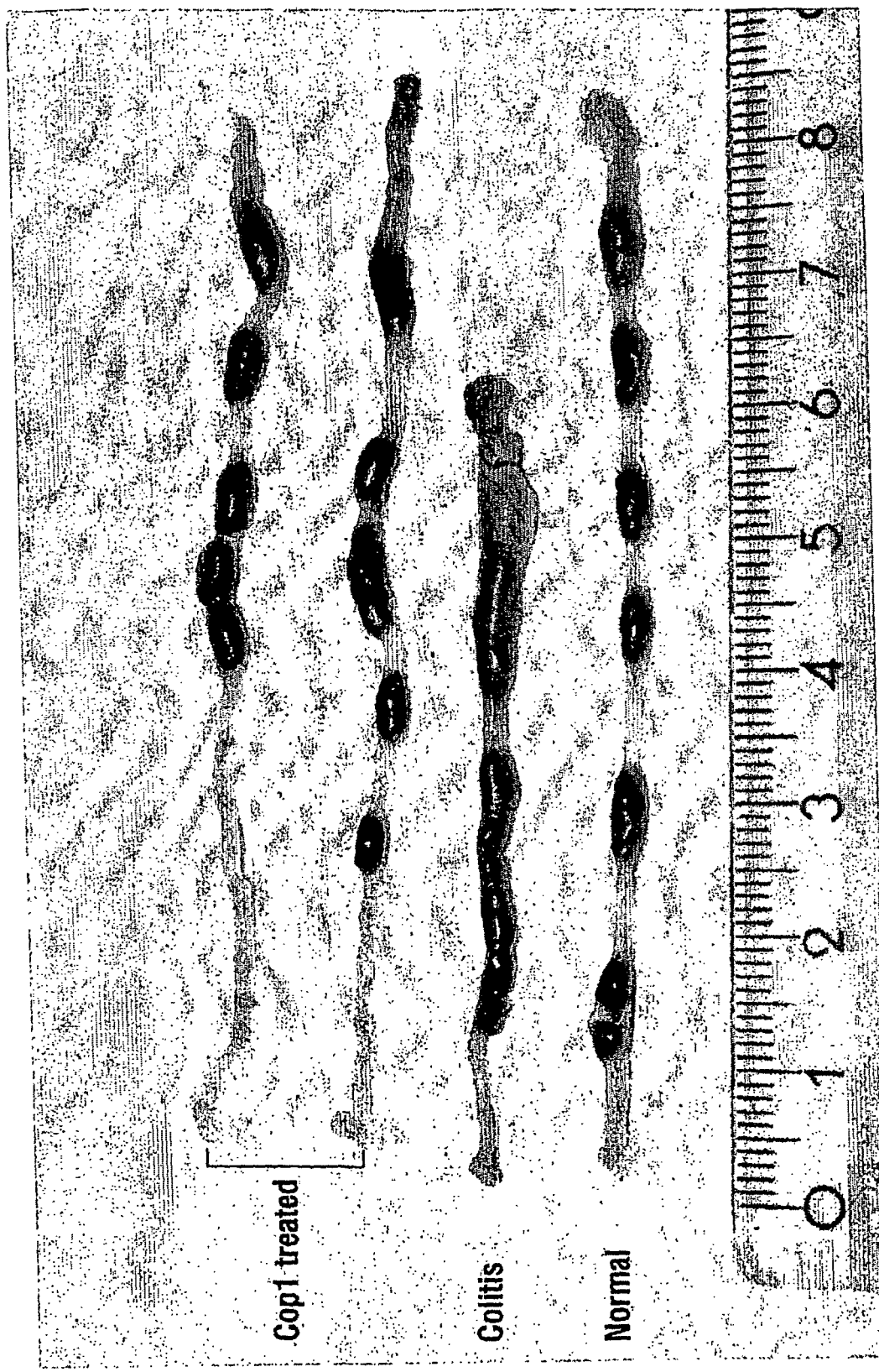
FIGS. 1A-1C show the effect of oral treatment of Cop 1 (glatiramer acetate, GA) on TNBS-induced colitis in BALB/c mice.

In recent years several studies were reported, describing the elucidation of the mechanism by which Copolymer 1 exerts its beneficial effect. It was thus demonstrated that Copolymer 1 binds promiscuously and with high affinity to various class II MHC molecules of mouse and human origin, and can even displace antigens from the MHC antigen-binding groove [Fridkis-Hareli et al., 1994]. In this way, the presentation of other antigens and, consequently, the persistence of inflammatory process, is down-regulated. In addition, Copolymer 1 was shown to be a potent inducer of regulatory T cells of the Th2 type (Aharoni et al., 1997). Moreover, it leads to deviation of the immune reactivity from Th1 to Th2 profile, in animals as well as humans (Aharoni et al., 1998; Neuhaus et al., 2000). In view of this immunomodulating activities of Copolymer 1 and the Th1-related immunopathological nature of Crohn's disease, it was of interest to test whether Copolymer 1 can be effective also in the suppression of inflammatory bowel diseases. Towards this end, we tested the effect of Cop 1 on the experimental animal model, namely the TNBS-induced murine model of colitis, that resembles human Crohn's disease in terms of its histopathological features and cytokine reactivity (Wirtz and Neurath, 2000).

It is shown herein, in accordance with the present invention, that, indeed, Cop 1, administered either orally or parenterally by daily injections, significantly ameliorates the various pathological manifestations of TNBS-induced colitis in three strains of mice, indicating that Cop 1 can be useful in treatment of inflammatory bowel diseases.

As used herein, the terms "Copolymer 1", "Cop 1", "Cop-1", "glatiramer acetate" and "GA" are each used interchangeably.

For the purpose of the present invention, "Cop 1 or a Cop 1-related peptide or polypeptide" is intended to include any peptide or polypeptide, including a random copolymer, that cross-reacts functionally with myelin basic protein (MBP) and is able to compete with MBP on the MHC class II in the antigen presentation.

A copolymer for use as active agent in the present invention may be a random copolymer comprising a suitable quantity of a positively charged amino acid such as lysine (K) or arginine (R), in combination with a negatively charged amino acid (preferably in a lesser quantity) such as glutamic acid (E) or aspartic acid (D), optionally in combination with a non-charged neutral amino acid such as alanine (A) or glycine (G), serving as a filler, and optionally with an amino acid adapted to confer on the copolymer immunogenic properties, such as an aromatic amino acid like tyrosine (Y) or tryptophan (W).

The copolymers for use in the present invention can be composed of L- or D-amino acids or mixtures thereof. As is known by those of skill in the art, L-amino acids occur in most natural proteins. However, D-amino acids are commercially available and can be substituted for some or all of the amino acids used to make the copolymers used in the present invention. The present invention contemplates the use of copolymers containing both D- and L-amino acids, as well as copolymers consisting essentially of either L- or D-amino acids.

In one embodiment, the active agent for use in the present invention comprises at least one random three- or four-amino acid copolymer comprising one amino acid selected from each of the four following groups: (a) lysine (K) and arginie (R); (b) glutamic acid (E) and aspartic acid (D); (c) alanine (A) and glycine (G); and (d) tyrosine (Y) and tryptophan (W).

In one preferred embodiment, the copolymer comprises a combination of the amino acids tyrosine, glutamic acid, alanine, and lysine, herein designated poly-YEAK, of net overall positive electrical charge, and is most preferably Copolymer 1, of the following molar ratio of the amino acids: about 0.14 glutamic acid, about 0.43 alanine, about 0.10 tyrosine, and about 0.34 lysine. It may be a low molecular weight or high molecular weight copolymer being a polypeptide from about 15 to about 100, preferably from about 40 to about 80, amino acids in length. The copolymer has an average molecular weight of about 2,000-40,000 Da, preferably of about 2,000-13,000 Da, more preferably of about 4,700-13,000 Da, most preferably of about 5,000-9,000 Da, and mostly preferred of about 6,000-8,000 Da. This preferred copolymer, Cop 1, is most preferably in the form of its acetate salt known under the generic name glatiramer acetate or GA. Preferred molecular weight ranges and processes for making a preferred form of Cop 1 are described in U.S. Pat. No. 5,800,808, the entire contents of which are hereby incorporated by reference in their entirety as if fully disclosed herein.

It is clear that this is given by way of example only, and that the active agent can be varied both with respect to the constituents and relative proportions of the constituents, thus obtaining poly-YEAK copolymers different from Cop 1.

In another embodiment, the active agent of the present invention is a Cop 1-related polypeptide that is a random copolymer containing four different amino acids, each from a different one of the groups (a) to (d), but excluding Cop 1. The activity exhibited by Copolymer 1 is expected to remain if one or more of the following substitutions is made in the amino acid composition of the copolymer: aspartic (D) acid for glutamic acid (E), glycine (G) for alanine (A), arginine (R) for lysine (K), and tryptophan (W) for tyrosine (Y).

Thus, in another embodiment, the Cop 1-related polypeptide of the invention may include any of those copolymers disclosed in WO 00/05250, the entire contents of which being hereby incorporated herein by reference as if fully disclosed herein, and other synthetic amino acid copolymers such as the random four-amino acid copolymers described by Fridkis-Hareli et al. (2002) as candidates for treatment of multiple sclerosis, namely copolymers (14-, 35- and 50-mers) containing the amino acids phenylalanine, glutamic acid, alanine and lysine (poly-FEAK), or tyrosine, phenylalanine, alanine and lysine (poly-YFAK), and any other similar copolymer to be discovered that can be considered a universal antigen similar to Cop 1.

In another embodiment, the Cop 1-related polypeptide of the invention is a copolymer containing a combination of three different amino acids each from a different one of three groups of the groups (a) to (d). These copolymers are herein referred to as terpolymers. In a more preferred embodiment, the mole fraction of amino acids of the terpolymers is about what is preferred for Copolymer 1.

In one embodiment, the terpolymers for use in the present invention contain tyrosine (Y), alanine (A), and lysine (K), hereinafter designated poly-YAK. The average molar fraction of the amino acids in these terpolymers can vary. For example, tyrosine can be present in a mole fraction of about 0.005-0.250; alanine can be present in a mole fraction of about 0.3-0.6; and lysine can be present in a mole fraction of about 0.1-0.5, but preferably the molar ratios of tyrosine, alanine and lysine are about 0.10 to about 0.54 to about 0.35. The average molecular weight of poly-YAK is about 2,000-40,000 Da, preferably about 3,000-35,000 Da, more preferably about 5,000-25,000 Da. It is possible to substitute arginine (R) for lysine (K), glycine (G) for alanine (A), and/or tryptophan (W) for tyrosine (Y).

In another embodiment, the terpolymers for use in the present invention contain tyrosine (Y), glutamic acid (E), and lysine (K), hereinafter designated poly-YEK. The average mole fraction of the amino acids in these terpolymers can vary: glutamic acid can be present in a mole fraction of about 0.005-0.300, tyrosine can be present in a mole fraction of about 0.005-0.250, and lysine can be present in a mole fraction of about 0.3-0.7, but preferably the molar ratios of glutamic acid, tyrosine, and lysine are about 0.26 to about 0.16 to about 0.58. The average molecular weight of poly-YEK is about 2,000-40,000 Da, preferably about 3,000-35,000 Da, more preferably about 5,000-25,000 Da. It is possible to substitute arginine (R) for lysine (K), aspartic acid (D) for glutamic acid (E), and/or tryptophan (W) for tyrosine (Y).

In a further embodiment, the terpolymers for use in the present invention contain lysine (K), glutamic acid (E), and alanine (A), hereinafter designated poly-KEA. The average molar fraction of the amino acids in these polypeptides can also vary. For example, glutamic acid can be present in a mole fraction of about 0.005-0.300, alanine in a mole fraction of about 0.005-0.600, and lysine can be present in a mole fraction of about 0.2-0.7, but preferably the molar ratios of glutamic acid, alanine and lysine are about 0.15 to about 0.48 to about 0.36. The average molecular weight of YEK is about 2,000-40,000 Da, preferably about 3,000-35,000 Da, more preferably about 5,000-25,000 Da. It is possible to substitute arginine (R) for lysine (K), aspartic acid (D) for glutamic acid (E), and/or glycine (G) for alanine (A).

In still another embodiment, the terpolymers for use in the present invention contain tyrosine (Y), glutamic acid (E), and alanine (A), hereinafter designated poly-YEA. The average molar fraction of the amino acids in these polypeptides can vary. For example, tyrosine can be present in a mole fraction of about 0.005-0.250, glutamic acid can be present in a mole fraction of about 0.005-0.300, and alanine can be present in a mole fraction of about 0.005-0.800, but preferably the molar ratios of glutamic acid, alanine, and tyrosine are about 0.21 to about 0.65 to about 0.14. The average molecular weight of poly-YEA is about 2,000-40,000 Da, preferably about 3,000-35,000 Da, and more preferably about 5,000-25,000 Da. It is possible to substitute tryptophan (W) for tyrosine (Y), aspartic acid (D) for glutamic acid (E), and/or glycine (G) for alanine (A).

The terpolymers can be made by any procedure available to one of skill in the art, for example as described in the above-mentioned publications WO 01/52878 and WO 01/93893.

As binding motifs of Cop 1 to MS-associated HLA-DR molecules are known, polypeptides of fixed sequence can readily be prepared and tested for binding to the peptide-binding groove of the HLA-DR molecules as described in Fridkis-Hareli et al. (1999). Examples of such peptides are those disclosed in WO 005249, the entire contents of which are hereby incorporated by reference as if fully disclosed herein. Thirty-two of the peptides specifically disclosed in said application are reproduced in Table I hereinbelow (SEQ ID NO:1 to NO:32). These are 15-mer peptides comprising the 4 amino acids alanine, glutamic acid, lysine and tyrosine (peptides 2, 3, 5-32) or only the 3 amino acids alanine, lysine and tyrosine (peptides 1, 4). Such peptides and other similar peptides would be expected to have similar activity as Cop 1 and are encompassed within the definition of Cop 1-related peptides or polypeptides of the invention.

TABLE 1

| SEQ ID NO. | Peptide Sequence |
| --- | --- |
| 1 | AAAYAAAAAKAAAA |
| 2 | AEKYAAAAAKAAAA |
| 3 | AKEYAAAAAKAAAA |
| 4 | AKKYAAAAAKAAAA |
| 5 | AEAYAAAAAKAAAA |
| 6 | KEAYAAAAAKAAAA |
| 7 | AEEYAAAAAKAAAA |

TABLE 1-continued

| SEQ ID NO. | Peptide Sequence |
| --- | --- |
| 8 | AAEYAAAAAAKAAAA |
| 9 | EKAYAAAAAAKAAAA |
| 10 | AAKYEAAAAAKAAAA |
| 11 | AAKYAEAAAAKAAAA |
| 12 | EAAYAAAAAAKAAAA |
| 13 | EKKYAAAAAAKAAAA |
| 14 | EAKYAAAAAAKAAAA |
| 15 | AEKYAAAAAAAAAA |
| 16 | AKEYAAAAAAAAAA |
| 17 | AKKYEAAAAAAAAA |
| 18 | AKKYAEAAAAAAAA |
| 19 | AEAYKAAAAAAAAA |
| 20 | KEAYAAAAAAAAAA |
| 21 | AEEYKAAAAAAAAA |
| 22 | AAEYKAAAAAAAAA |
| 23 | EKAYAAAAAAAAAA |
| 24 | AAKYEAAAAAAAAA |
| 25 | AAKYAEAAAAAAAA |
| 26 | EKKYAAAAAAAAAA |
| 27 | EAKYAAAAAAAAAA |
| 28 | AEYAKAAAAAAAAA |
| 29 | AEKAYAAAAAAAAA |
| 30 | EKYAAAAAAAAAAA |
| 31 | AYKAEAAAAAAAAA |
| 32 | AKYAEAAAAAAAAA |

In accordance with the present invention, the candidate active agent is tested in a suitable animal model for inflammatory bowel disease such as the TNBS-induced colitis murine model, that has been very useful for the study of many important aspects of inflammatory bowel disease. Since this model, by itself, does not represent the complexity of the human diseases, more than 20 novel animal models of intestinal inflammation have been developed in recent years (Bregenholt, 2000; MacDonald et al., 2000; Wirtz and Neurath, 2000). They can be divided into four categories: (i) spontaneous models, such as the colitis in C3H/HeJBir mice, a new substrain of C3H/HeJ mice with a high incidence of spontaneous colitis; (ii) inducible models in mice with a normal immune system, such as the dextran sulfate sodium (DSS) colitis; (iii) adoptive transfer models in immunocompromised host, such as the CD45RB CD62L+ cells into SCID mice; and (iv) genetically-engineered models, such as the IL-10 knockout mice. Although most models have very heterogeneous origin, most of them result in a common phenotype: mucosal inflammation mediated by Th1 T-cells that are activated by bacterial antigens in the mucosa, a manifestation that is very similar to human Crohn's disease. All of these models can be used according to the invention.

According to the present invention, the preferred copolymer for use as the active agent of the invention is Cop 1, most preferably in the form of its acetate salt known under the generic name glatiramer acetate. The dosage of Cop 1 to be administered will be determined by the physician according to the age of the patient and stage of the disease and may be chosen from a range of 0.1 to 1,000 mg, although any other suitable dosage is encompassed by the invention. The administration may be made daily in one or more doses, preferably from one to three daily doses, for example in a total of 0.1 to 1,000 mg, or in alternate days, three times a week, or once a week, but any other suitable interval between the administrations is envisaged by the invention according to the severity of the disease and the condition of the patient.

The composition of the invention may be administered by any suitable mode of administration including orally, by inhalation, intramuscularly, subcutaneously or intradermally.

Oral administration may be a preferred form of administration, both because it is preferred by patients and because, in IBD, this route has additional advantages of specific administration into the diseased organ and, consequently, activation of local beneficial mechanisms such as MHC blocking in addition to the systemic activity.

In a preferred embodiment, the composition is administered orally. In this case, Cop 1 may be mixed with other food forms and consumed in solid, semi-solid, suspension or emulsion form, and it may be mixed with pharmaceutically acceptable carriers, including water, suspending agents, emulsifying agents, flavor enhancers, and the like, or it may be in liquid form, aerosol, inhalable powder or solid form, preferably enterically-coated form, all as described in WO 98/30227 and corresponding U.S. Pat. No. 6,214,791, hereby incorporated by reference in its entirety as if fully disclosed herein.

In another preferred embodiment, Cop 1 is administered parenterally, preferably subcutaneously.

The following examples illustrate certain features of the present invention but are not intended to limit the scope of the present invention.

EXAMPLES

Materials and Methods

Animals. BALB/c, SJL/J, (SJL/JXBALB/c)F1 and C57BL/6 mice were purchased from Harlan (Jerusalem, Israel). Female mice, 8-12 week of age, weighing 18-21 g, were used in all experiments.

Materials. Glatiramer acetate (GA, Copaxone™, Copolymer 1) from batch 242990599, with an average molecular weight of 7300 kDa, was obtained from Teva Pharmaceutical Industries Ltd. (Petach Tikva, Israel). 2,4,6-Trinitrobenzenesulfonic acid (TNBS) was from Sigma. Immobilized anti-CD3 antibody is from Serotec.

Induction of cholitis in mice. TNBS-colitis was induced by rectal instillation of 2,4,6-trinitrobenzene sulfonic acid 5% (w/v), mixed with an equal volume of ethanol, into anesthetized mice (100 μl/mouse). Each treatment group included 6-12 mice. Mice that died before day 4 were considered as treatment casualties and were not taken into consideration.

Assessment of colitis. Weight changes and survival were monitored daily. Five to eight days following TNBS instillation, mice were sacrificed and macroscopic as well as microscopic colonic damage was evaluated.

Macroscopic colonic scoring. Gross colonic damage was graded according to Reuter et al. (1996), using the combined values of the four standard macroscopic parameters: degree of colonic ulcerations (scale from 0—completely normal, to 10—most severe); intestinal and peritoneal adhesions (0 to 2); diarrhea (0 to 1); and thickness (0 to 1). The total score is the arithmetic sum of the four scores. The evaluation was performed in a blind procedure.

Microscopic scoring. Proximal, medial, and distal portions of colon were fixed in 10% phosphate-buffered formalin. Paraffin-embedded sections were stained with hematoxylin and eosin. The degree of histological damage and inflammation was graded according to Elson et al. (1996) using the combined values of the four microscopic parameters: extent (scale from 0—completely normal, to 2—involving more than one segment); inflammation (0—none to 3—severe); damage (0 to 3—severe transmural); and regeneration (0—complete re-eptihelization to 3—none). The total score is the arithmetic sum of the four scores. The evaluation was performed in a blind procedure.

Histological examination. Colons removed as described above were fixed in formalin, and histological evaluation was performed on the fixed colon samples stained with hematoxilin-eosin. The samples were examined by a pathologist and ranked from 0 to 6 by the degree of inflammatory infiltrate, ulceration or necrosis, and the depth and surface extension of the lesion.

GA treatment. GA was administered by one of the following procedures:

Oral treatment—250 μg/day in PBS, fed by gastric intubation with an 18-gauge stainless steel feeding needle. Unless otherwise stated, feedings were performed on days-7, -5, -3, -1, 0, 2, 4 and 6, relative to the day of TNBS instillation.

Parenteral treatment by daily injections—2.5 mg/day, administered subcutaneously in PBS, starting 14 days before disease induction.

Single injection—A depot dose of 10 mg/mouse, injected subcutaneously in incomplete Freund's adjuvant (ICFA), 14 days before disease induction.

Colon extract. Colons of syngeneic normal mice were cut into small strips and homogenized. The homogenate was diluted in PBS and passed through glass wool. Protein quantity was measured by using a protein assay kit (Bio-Rad, Richmond, Calif.).

Reactivity assays. Spleens and mesenteric lymph nodes (MLN) cells ($0.5 \times 10^6$ cell/well) were cultured with either GA (50 μg/ml), colon extract (200 μg/ml), immobilized anti-CD3 (5 μg/ml), or PBS control, in a final volume of 250 μl/well (6 wells for each antigen). For proliferation assay, cells were cultured in RPMI 1640 with 10% FCS, pulsed with 1 μCi of [3H] thymidine after 48 h incubation, and harvested 12 h later. For cytokine (TNF-α and TGF-β) assay, cells were cultured in serum-free medium (DCCM-1), supernatants were collected after 72 h, and tested for the cytokines by ELISA using mAbs pairs (R&D Systems, Minneapollis, Minn.) according to the manufacturer's instruction.

Statistical analysis. Macroscopical and microscopical scores, as well as weight differences between GA-treated and untreated groups, were analyzed using two-tailed Mann-Whitney U test. Statistics of survival curves were performed by Kaplan-Meier test. Differences in proliferation responses, TNF-α and TGF-β secretion were compared using the two-tailed independent t-test. All the statistical tests were performed by the SPSS 10.0 program. The level of significance for all the tests was set at $<0.05$.

Example 1

Effect of Oral Treatment of Cop 1 on TNBS-Induced Colitis in BALB/c Mice

Colitis was induced by TNBS in 50% ethanol. GA was administered orally (250 μg/mouse per feeding) every other day, starting either seven or three days before induction of disease, at the day of induction, as well as two days after the induction, and was continued as indicated in Table 2B below, left row. Colonic scoring was performed 7 or 8 days after disease induction. Mice that died during the first 2 days (usually around 20% in all groups) were considered as treatment casualties and thus are not presented; each group contained 4-7 mice that survived after day 2.

The first set of experiments tested the ability of orally administered GA (250 µg/mouse, at alternate days, starting 7 days before disease induction, 8 feedings) to ameliorate experimental TNBS-induced colitis in BALB/c mice. Macroscopic evaluation of colons from GA fed, versus those of control mice, in three different experiments, revealed that GA treatment led to drastic reduction in the colonic damage characteristic to the disease, as summarized in Table 2A. Thus, the various macroscopic pathological manifestations, i.e. severe ulceration and/or inflammation, adhesion to adjacent organs, diarrhea and bowel wall thickening were all significantly reduced (3.5 to 4.0 fold average in the three experiments) by GA treatment. The total macroscopic damage, obtained by the arithmetic sum of the scores of all four pathological manifestations, was decreased from 10.2 in the control to 2.7 in the GA-treated groups, namely by 3.8 fold.

Representative colons from normal mouse as well as a mouse with TNBS-induced colitis graded 8 (ulceration/inflammation at two sites, major adhesions, diarrhea and bowel thickness), versus colons from two TNBS-induced mice treated orally with GA and graded 1 (focal hyperemia only), are demonstrated in FIG. 1A. As shown, GA treatment led to a marked reduction of the macroscopic colonic damage induced by TNBS.

GA was particularly effective, when feedings started seven days before TNBS inoculation and continued after disease induction (total of 8 feedings every other day). Under these conditions 5.2 fold reduction in disease severity was achieved (Table 2B). However, a significant beneficial effect was observed also when GA treatment started only three days before induction (2.75 fold reduction), or on the day of TNBS inoculation, and even two days after disease induction (2.2 fold reduction).

Figure 1B:
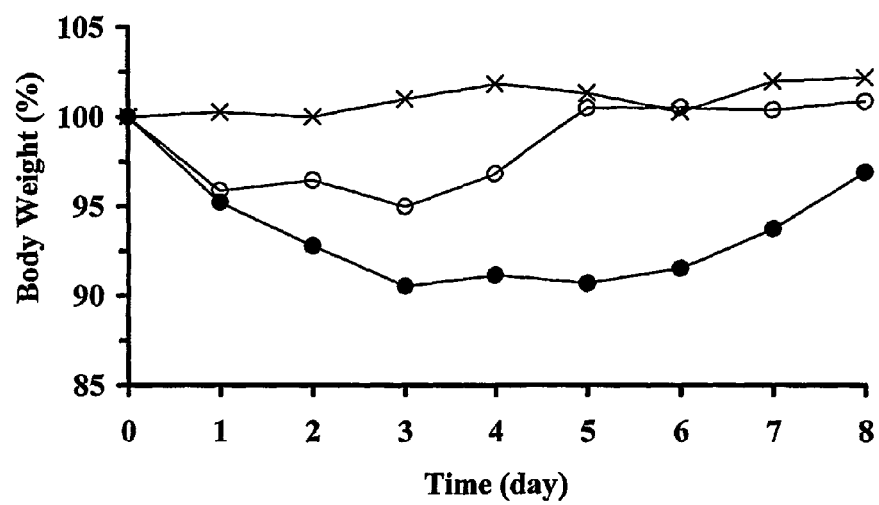

Weight loss is a characteristic of colitis. BALB/c mice with TNBS-induced colitis manifested considerable weigh loss (10% of their body weight, by day 3 after TNBS inoculation), starting to recover from day 7 but not returning to their original weight, as shown in FIG. 1B. Mice fed with GA suffered only moderate weight loss (maximum 5% of their body weight by day 3) and subsequently exhibited weight regain till complete restoration of their original weight by day 5. Thus, GA-treated mice exhibited significantly higher weights than those of the untreated mice, and 5-8 days after disease induction their weight curve was similar to that of normal mice, which had not been induced with disease.

Figure 1C:
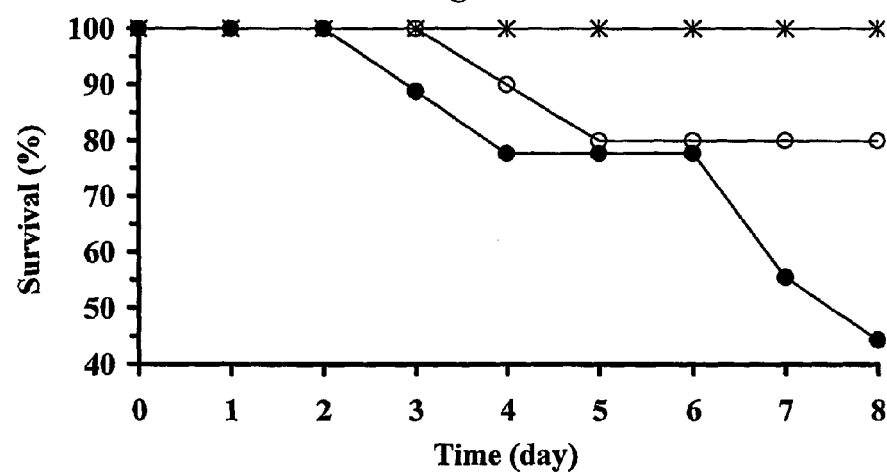

In all groups approximately 20% died in the first two days after TNBS instillation. They were considered treatment casualties and were excluded from all calculations or presentation. The mortality from the disease exceeded 55% in the untreated mice, 8 days after induction, whereas only 20% mortality was observed in the GA-treated mice due to the disease process (FIG. 1C). Thus, oral treatment of BALB/c mice with GA resulted in improved survival rate, in addition to the reduced manifestations of TNBS-induced colitis.

Figure 2:
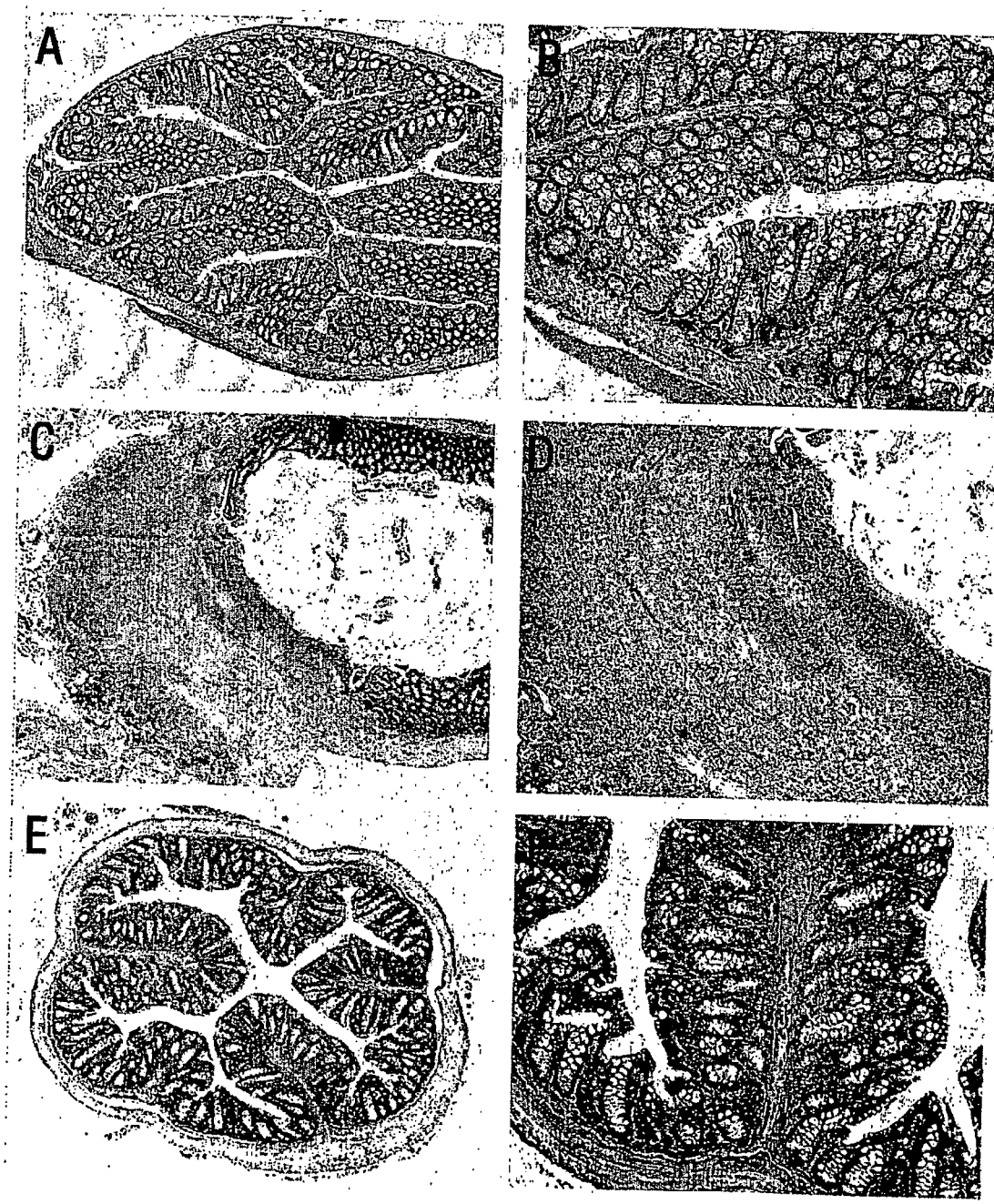
FIGS. 2A-2F are photographs of histological samples showing the effect of GA treatment on the microscopic manifestations of TNBS-induced colitis. Histological features of representative colonic sections from BALB/c mice, 7 days after administration of TNBS are demonstrated. Normal colon—2A (original magnification ×40) and 2B (×100); TNBS-induced control colon showing complete mucosal ulceration, intense transmural inflammation, extensive ulceration and disruption of the normal intestine architecture—2C (×40) and 2D (×100); Colon of TNBS induced mouse treated orally with GA demonstrating almost normal sections, preserved mucosa, normal glandular structure, with only mononuclear cells infiltration in submucosa and crypts—2E (×40) and 2F (×100).

Histological assessment of colonic specimens from the mice with TNBS-induced colitis not treated with GA revealed severe mucosal damage, focal extension of inflammation accompanied with transmural inflammation, extensive ulceration and severe disruption of the normal architecture (FIGS. 2C, 2D). In contrast, colons of TNBS-induced mice treated with GA demonstrated more preserved mucosa (FIG. 2E), and only rare mononuclear cells infiltration in submucosa and crypts (FIG. 2F). The intestine architecture of the GA-treated mice was much less damaged and the glandular structure was well conserved (FIG. 2E, 2F), similar to that of normal mice intestine (FIGS. 2A, 2B). The average histological score of mice surviving till day 7 in which histological samples were collected was 7.8 in the colitis group and 2.8 in the GA treatment group (from a maximal score of 12.0), indicative of 2.8 folds reduction (p=0.007). GA treatment without TNBS induction did not result in any histological or macroscopic damage.

Example 2

Effect of Various GA Treatment Modes on TNBS-Induced Colitis in Different Mouse Strains To explore whether the beneficial effect of GA on TNBS-induced colitis is restricted to oral administration in the BALB/c strain or represents a more general effect, we studied the ability of GA administered by different routes and dosages to inhibit TNBS-induced colitis in two additional strains of mice. Hence, the effects of oral treatment (250 µg/feeding, at alternate days, starting 7 days before disease induction); a single injection of a depot dose (5 mg/mouse subcutaneous (SC) in ICFA, 14 days before induction); or daily injections (2.5 mg/mouse SC in PBS, starting either 7 or 14 days before induction) were tested in the SJL/J strain and the F1 hybrid strain of SJL/J and BALB/c-(SJL/JxBALB/c)F1.

Macroscopic evaluation of the colons, as summarized in Table 3, revealed that, similarly to the BALB/c strain, both strains are highly susceptible to TNBS colitis (100% disease incidence in the untreated control groups). Particularly sensitive were the SJL/J mice in which a score of 12.4 was found from maximum total score of 14. The aggressive disease in the SJL/J strain was accompanied by the manifestation of particularly small spleens and exceptionally enlarged MLN. Oral treatment with GA reduced the macroscopic damage induced by the disease in both strains, (although to a lesser extent than in the BALB/c, Table 1). Thus, 1.8 and 1.7 fold decrease in the total macroscopic damage was found in (SJL/JxBALB/c)F1 mice fed with GA in comparison to untreated mice, observed 5 and 11 days after TNBS inoculation, respectively. In SJL/J mice, which manifested the most severe disease, only minor effect of oral treatment with GA was obtained (a decrease of 1.7 Points in the total score). On the other hand, GA treatment administered by daily injections was more effective than oral treatment and drastically reduced the colonic damage characteristic to the disease. Thus, 5 days after disease induction, 3.5- and 4.6-fold decrease in the total macroscopic score were obtained in (SJL/JxBALB/c)F1 mice injected from day-7 and -14, respectively, in comparison to untreated mice. An even more pronounced effect was obtained 11 days after disease induction when mice injected daily with GA demonstrated almost complete recovery (only one from seven mice showed focal hyperemia in each group resulting in total score of 0.1), while most of the untreated control mice were still sick (total score—5.3). Furthermore, significant reduction in macroscopic score by daily injections of GA was obtained even in SJL/J mice, which exhibited the most severe disease (2.7-fold reduction in comparison to untreated control by injections from day-7), accompanied by normal appearance of spleens and MLN. A single injection of GA as a depot dose in ICFA was not sufficient to effectively prevent the macroscopic damage induced by TNBS inoculation. Although the macroscopic scores obtained by this treatment were lower than that of the untreated controls, this effect was small and statistically insignificant.

As shown in FIGS. 3A-3B, TNBS-induced colitis in both strains resulted in considerable weight lost. Hence, 2 days after induction, 12% and 15% weight reduction was observed in (SJL/JxBALB/c)F1 (A) and SJL/J (B) mice receiving no treatment. Yet, while the F1 mice exhibited subsequent weight regain (restoring 95% of their initial weight by day 6), the SJL/J mice continued to lose weight till day 4, and their average weight on day 5 was only 80% of their initial weight. GA treatments partially inhibited the extent of weight loss caused by the TNBS colitis in both strains. This was manifested in a modest, statistically insignificant, inhibition of weight loss in the orally-treated mice and in a major significant inhibition of weight loss in the daily-injected mice. For example, (SJL/JxBALB/c)F1 mice injected daily (from day-7) lost only 4% of their original weight, 1 day after induction, and subsequently recovered showing complete weight restoration by day 6. In both strains, the F1 which expresses the milder disease, as well as in the SJL/J which expresses the more severe disease, body weights of mice injected daily with GA were significantly higher than those of untreated mice ($p<0.01$).

Figure 3C:
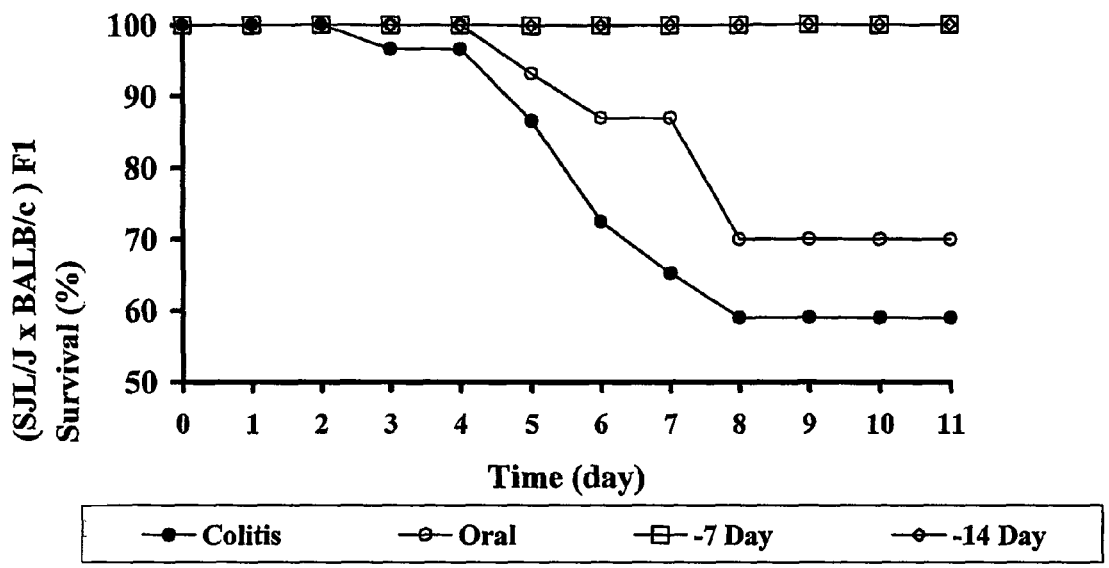
Figure 3D:
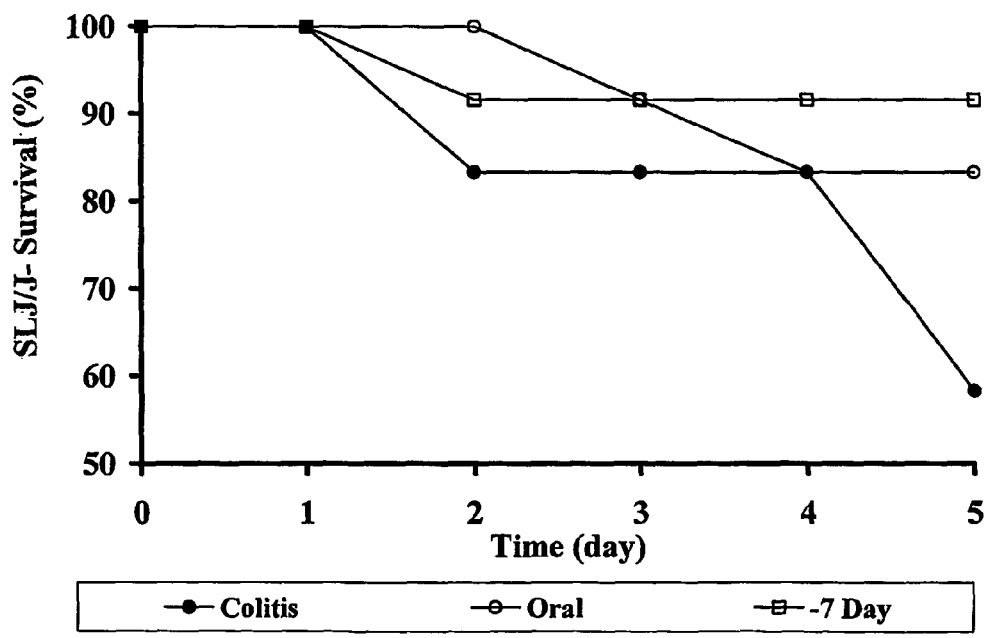

The mortality from the disease exceeded 40% in the untreated mice in both strains (by day 8 in the (SJL/JxBALB/c)F1, and by day 5 in the SJL/J mice), whereas mortality rates of only 30% and 18%, respectively, were observed after oral treatment with GA in these two groups (FIGS. 3C, 3D). Furthermore, daily injection of GA (starting both 7 and 14 days before disease induction) completely prevented mortality in the (SJL/JxBALB/c)F1 and only 8% succumbed in the SJL/J group ($P<0.05$ for both strains), indicating that GA essentially prevented mortality due to the disease process, significantly improving survival rates.

Figure 3E:
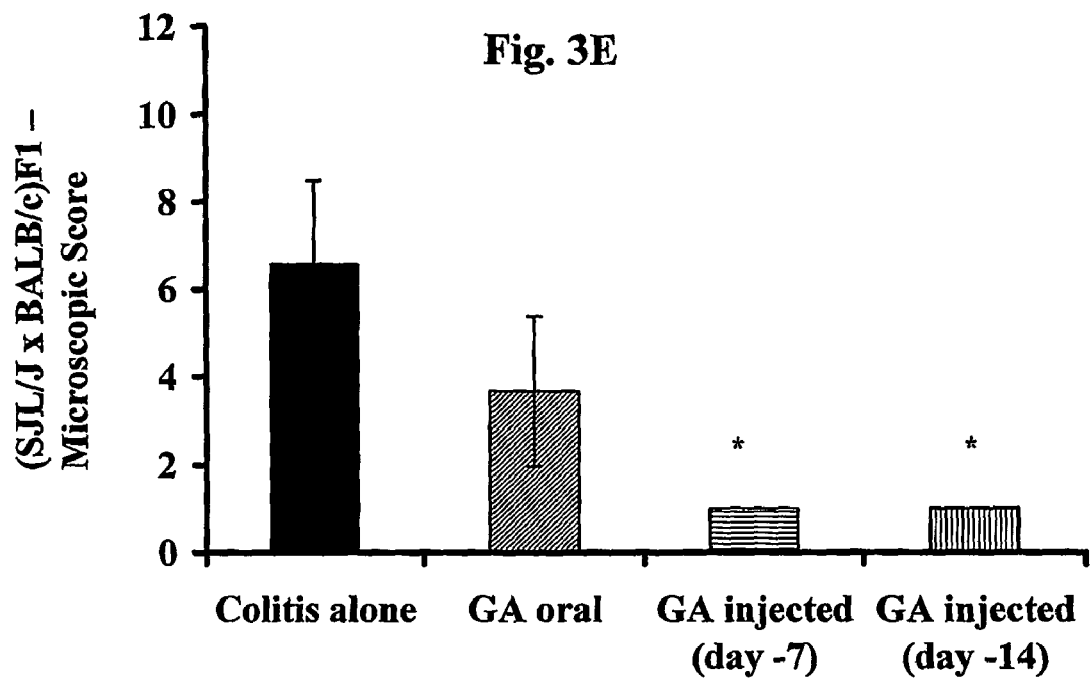
Figure 3F:
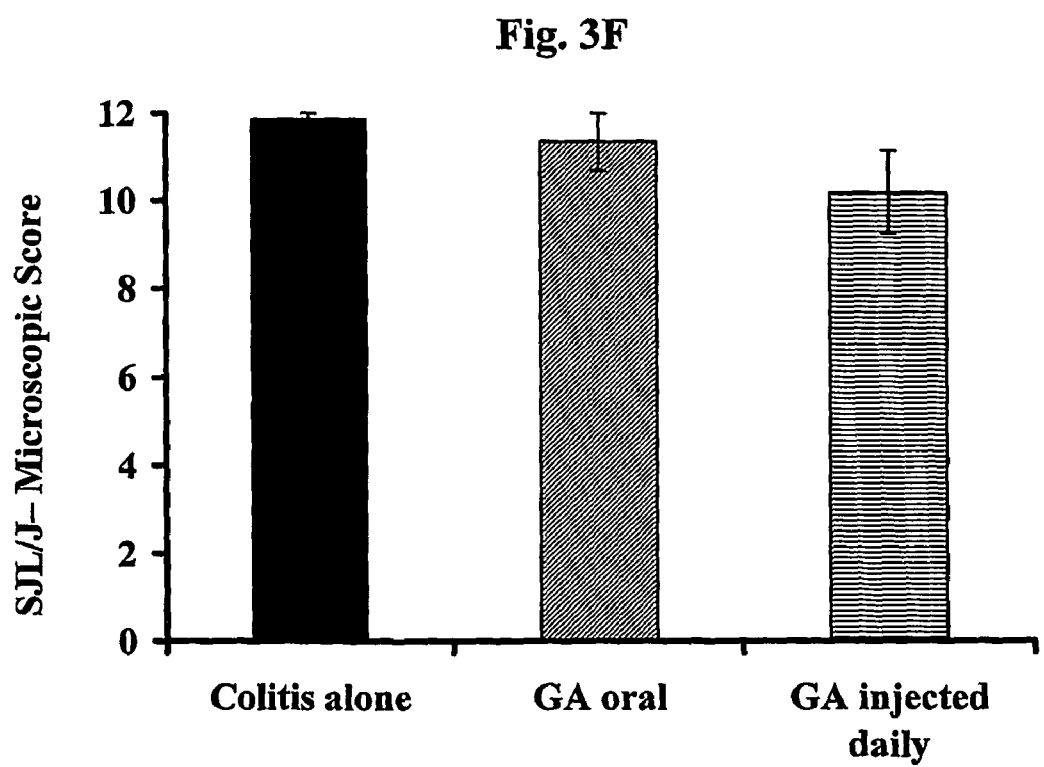

GA was also effective in preventing the microscopical colonic damage induced by TNBS colitis, as shown in FIGS. 3E and 3F. Thus, in (SJL/JxBALB/c)F1 mice, a reduction of 1.8-fold in the histological score was obtained by oral treatment, and 6.6-fold by daily injections (starting either 7 or 14 days before disease induction). In SJL/J mice, which manifested the most severe disease, only minor, statistically insignificant, effect of GA treatment was obtained (a decrease of 0.5 and 1.8 points in the total score by feeding and injection, respectively).

Example 3

The Effect of GA on Lymphocyte Reactivity of TNBS-Induced Colitis

Figure 4E:
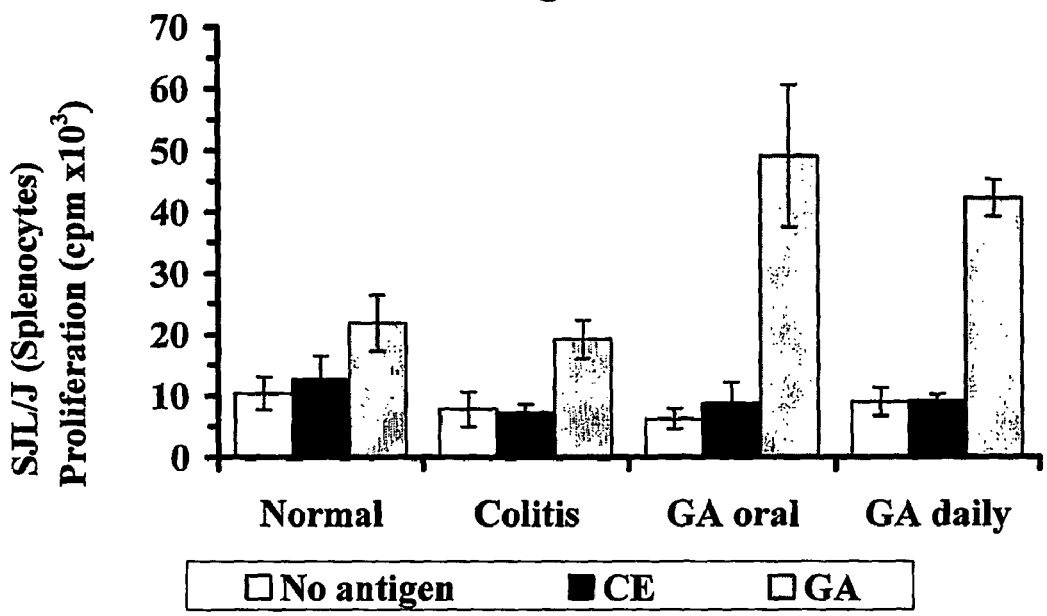
Figure 4F:
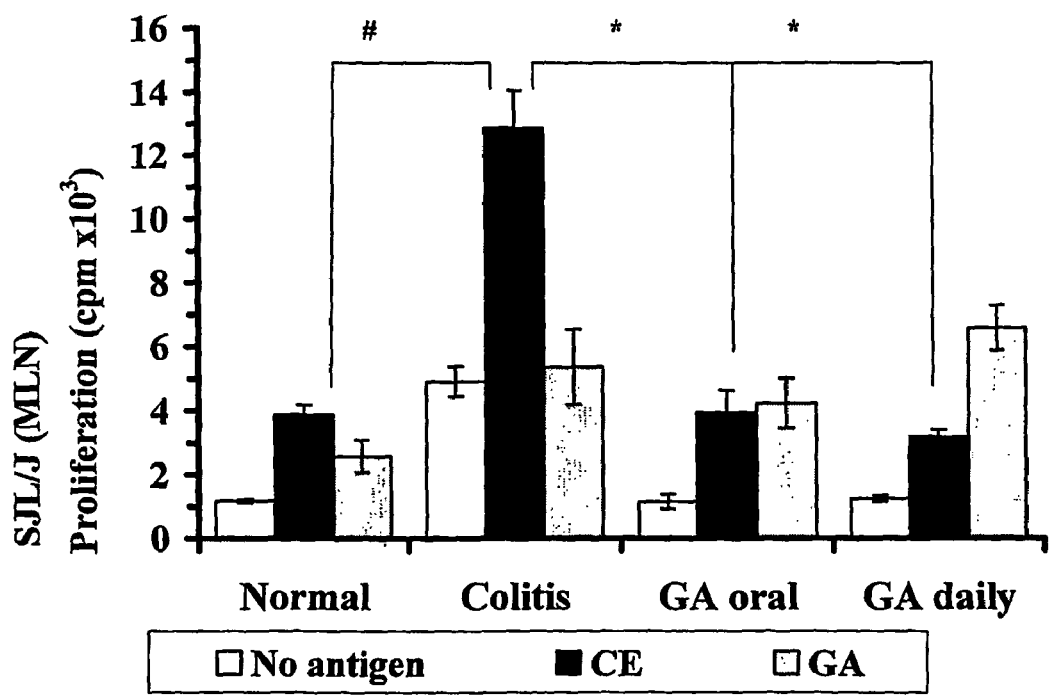

To investigate the effect of GA treatment on the T-cell reactivity in TNBS-induced colitis, we studied the cell proliferation response and the secretion of the cytokines TNF-$\alpha$ and TGF-$\beta$ in the colitis-induced mice treated with GA, as compared to the untreated mice. The reactivity of spleen cells—systemic response, as well as the reactivity of the local mesenteric lymph nodes (MNL), adjacent to the diseased organ, were analyzed in the three mice strains. The proliferation in response to colonic extract obtained from normal syngeneic mice (CE) and to GA, is demonstrated in FIGS. 4A-4F. A prominent proliferation response to colonic extract was demonstrated by MLN cells, i.e., 8.9, 2.0 and 3.3-fold in colitis induced mice over the response of normal MLN, in BALB/c (FIG. 4B), (SJL/JxBALB/c)F1 (FIG. 4D) and SJL/J (FIG. 4F), respectively ($P<0.05$). This reactivity was restricted to the local MLN, since no significant proliferation to CE, over the response of the same cells without antigen, was observed systemically (FIGS. 4A, 4C, 4E). This local response to the colonic extract was markedly inhibited by GA treatment, as manifested by 66% inhibition in MLN from BALB/c. Moreover, MLN from (SJL/JxBALB/c)F1 and SJL/J mice treated either orally or parenterally with GA, responded to CE similarly to MLN from normal mice, indicating complete inhibition of the response to colonic extract by GA treatment. Lymphocytes from GA-treated mice, from both spleens and MLN, proliferated in response to the treatment agent GA, the systemic response being considerably higher than the response of the MLN cells.

Figure 5A:
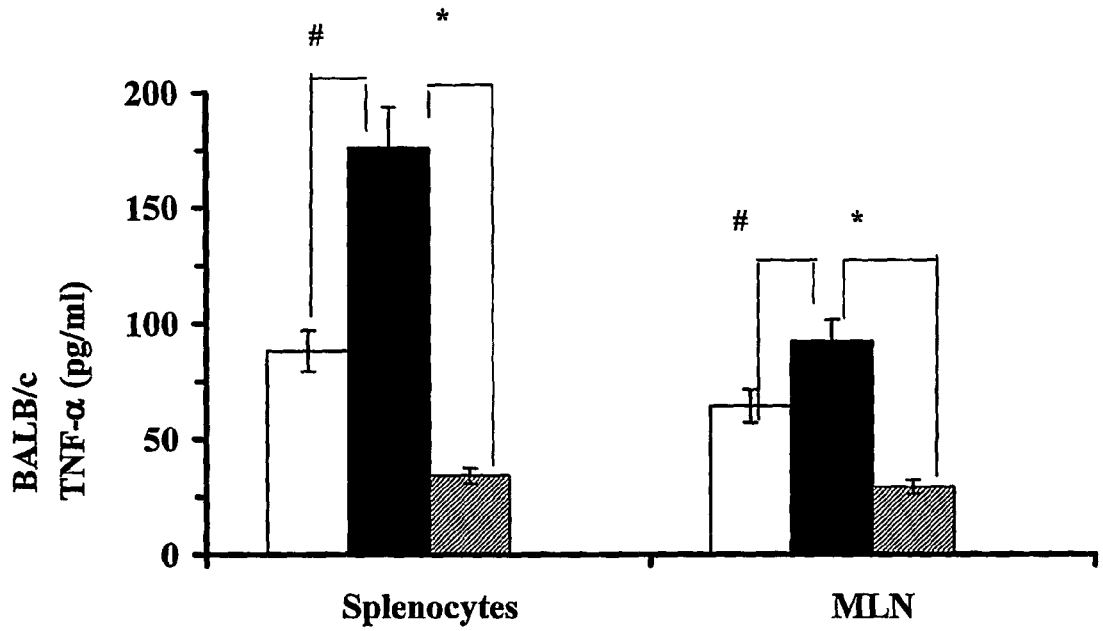
Figure 5B:
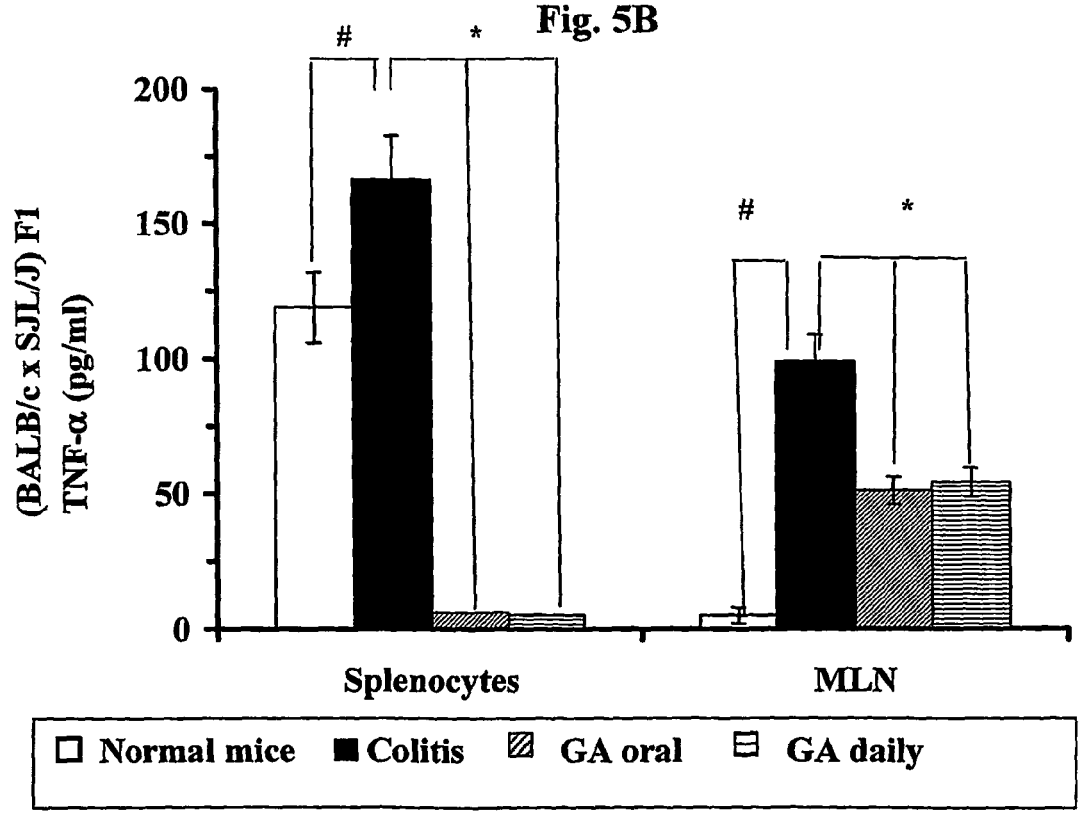

Cells from mice with TNBS-induced colitis secreted high amounts of TNF-$\alpha$, as detected by the response towards the broad stimulant anti-CD3. As shown in FIGS. 5A and 5B, in both BALB/c and (SJL/JxBALB/c)F1 mice this elevation was more pronounced in splenocytes than in cells from MLN. In contrast, SJL/J mice did not manifest such systemic elevation (FIG. 5C); however, the TNF-$\alpha$ secretion of their MLN cells was greatly increased. GA treatment in all strains resulted in substantial reduction in TNF-$\alpha$, in both spleens and MLN, so that the secretion levels in colitis-induced mice treated with GA were even lower than in normal mice. This reduction in TNF-$\alpha$ was found in all the instances, except in the MLN of SJL/J mice treated orally with GA, which did not manifest significant reduction in the pathological manifestations either. Yet, SJL/J mice parenterally treated daily with GA still demonstrated drastic decrease in TNF-$\alpha$ levels, as well as reduced disease score. In vitro stimulation by either GA or CE did not result in secretion of TNF-$\alpha$.

Figure 6A:
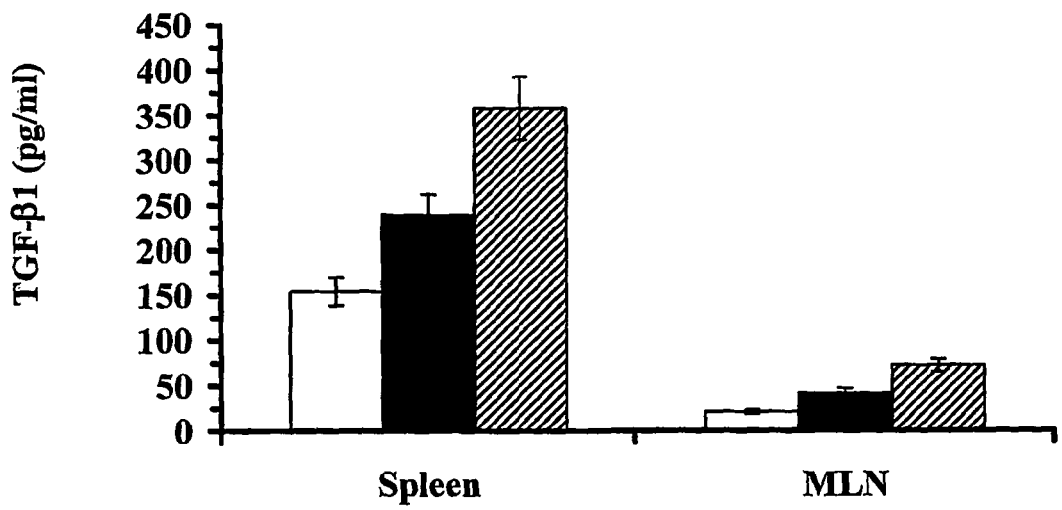
FIGS. 6A-6B show the effect of GA treatment on TGF-β secretion by lymphocytes of TNBS-induced BALB/c mice. Cells of spleen or mesenteric lymph nodes (MLN) from normal mice, colitis-induced mice, and colitis-induced mice treated with GA were cultured either with GA (50 µg/ml) (FIG. 6A) or immobilized anti-CD3 (5 µg/ml) (FIG. 6B). After 72 hours, supernatants from six culture wells were pooled and TGF-β was measured by ELISA in duplicates. Results are expressed as TGF-β concentration (pg/ml±1 SD) and represent one of two similar experiments, using pooled cells from 3-5 mice in each group. # Indicates significant decrease in TGF-β in colitic mice in comparison to normal mice. * Indicates significant increase in TGF-β induced by GA treatment in comparison to untreated colitis induced mice.
Figure 6B:
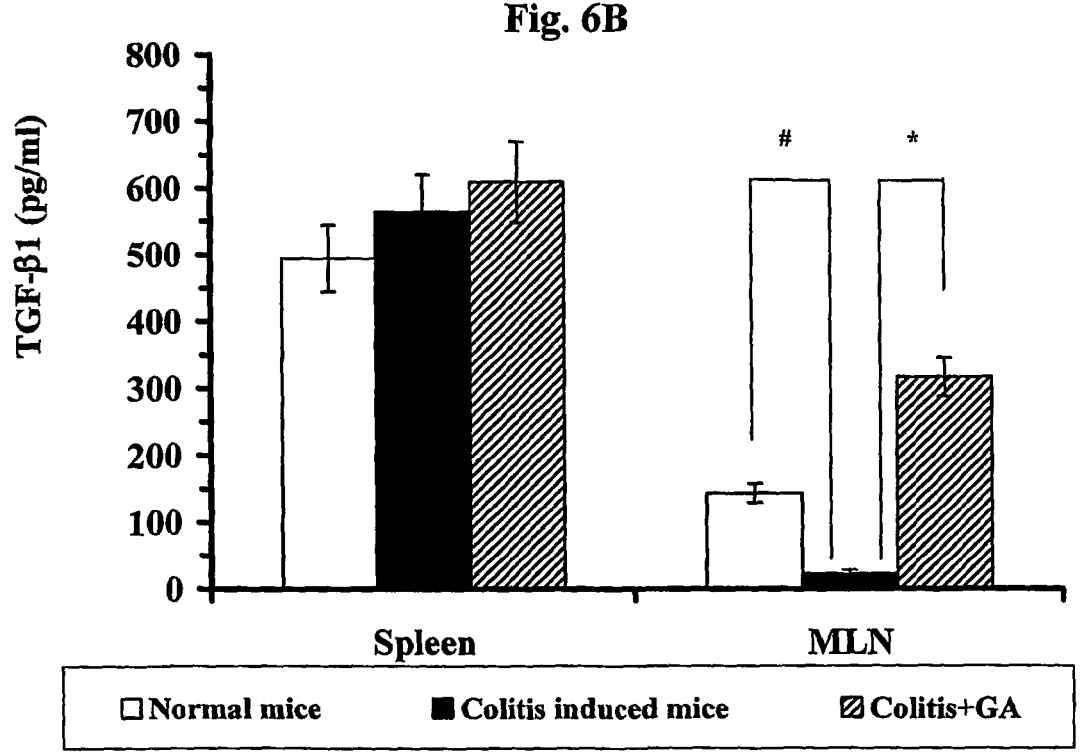

Secretion of TGF-$\beta$ in response to treatment with GA as well as to a broad stimulus by anti-CD3, was also evaluated. The results obtained in BALB/c mice are demonstrated in FIGS. 6A-6B. Spleen cells and to a lesser extent MLN cells secreted TGF-$\beta$ in response to GA. This response was more pronounced in mice treated with GA (FIG. 6A). Anti-CD3 stimulation resulted in the secretion of excessive amounts of TGF-$\beta$ by spleen cells of normal mice as well as those with colitis (FIG. 6B). Interestingly, in the MLN, secretion of TGF-$\beta$ was significantly reduced in colitis-induced mice (6.5 folds reduction in comparison to MLN of normal mice), but GA treatment generated prominent elevation of TGF-$\beta$ secretion in the MLN (2.2 folds higher than the secretion of normal mice). Similar results were obtained in (SJL/JxBALB/c)F1 mice, but not in SJL/J mice which manifested the most aggressive disease manifestations (results not shown).

Example 4

Effect of Cop 1 on Dextran Sulfate Sodium (DSS)-Induced Colitis in Mice

Feeding mice for several days with dextran sulfate sodium (DSS) polymers in the drinking water induces an acute colitis with bloody diarrhea, histological damage, and inflammation (Wirtz and Neurath, 2000).

Female C57BL/6, 7 weeks old mice, were fed with 2.5% DSS solution in the drinking water for 7 days. GA was administered subcutaneously by daily injections—2.5 mg/day, in PBS, starting either 7 days before or in the same day of DSS feeding.

The results of a preliminary experiment using this model are shown in FIG. 7. It was found that DSS-fed untreated mice suffered considerable weight loss from day 5, and lost 17% of their body weight by day 7 after DSS feeding. Mice treated with GA suffered only moderate weight loss (maximum 7% in mice injected from day-7, and 4% in mice injected from day 0, by day 7). These results indicate that GA might have a beneficial effect in DSS-induced colitis as well.

TABLE 2

The effect of oral treatment with GA on the macroscopic manifestations of TNBS-induced colitis in BALB/c mice

A. GA treatment starting seven days before disease induction

| | | | Macroscopic scoring of colon damage | | | | |
|---|---|---|---|---|---|---|---|
| Exp. No. | Treatment | N | Ulceration (max 10) | Adhesion (max 2) | Diarrhea (max 1) | Thickness (max 1) | Total Score (max 14) |
| 1 | Control | 5 | 6.8 | 1.6 | 0.4 | 0.4 | 9.2 |
|   | GA | 4 | 1.0 | 0.6 | 0.0 | 0.0 | 1.6* |
| 2 | Control | 4 | 7.4 | 1.8 | 0.9 | 0.4 | 10.5 |
|   | GA | 4 | 3.4 | 0.5 | 0.5 | 0.0 | 4.4* |
| 3 | Control | 7 | 8.3 | 1.4 | 0.7 | 0.6 | 11.0 |
|   | GA | 5 | 2.0 | 0.1 | 0.0 | 0.0 | 2.1* |
| Average | Control | 16 | 7.5 | 1.6 | 0.7 | 0.4 | 10.2 |
|   | GA | 13 | 2.1 | 0.4 | 0.2 | 0.0 | 2.7* |
|   | GA no colitis | 2 | 0.0 | 0.0 | 0.0 | 0.0 | 0.0 |

TABLE 2-continued

The effect of oral treatment with GA on the macroscopic manifestations of TNBS-induced colitis in BALB/c mice

B. Effect of timing of GA treatment in respect to disease induction

| | Macroscopic scoring of colon damage | | | | |
|---|---|---|---|---|---|
| Treatment | Ulceration (max 10) | Adhesion (max 2) | Diarrhea (max 1) | Thickness (max 1) | Total Score (max 14) |
| Control | 8.3 | 1.4 | 0.7 | 0.6 | 11.0 |
| GA starting day −7, 8 feedings | 2.0 | 0.1 | 0.0 | 0.0 | 2.1* |
| GA starting day −3, 8 feedings | 3.5 | 0.5 | 0.0 | 0.0 | 4.0* |
| GA starting day 0, 8 feedings | 4.3 | 0.7 | 0.0 | 0.0 | 5.0* |
| GA starting day +2, 6 feedings | 4.7 | 0.3 | 0.0 | 0.0 | 5.0* |

Colitis was induced in BALB/c mice by TNBS in 50% ethanol. GA was administered orally (250 μg/mouse), every other day, starting from the indicated day relatively to disease induction. Colonic scoring was performed 7 or 8 days after disease induction. Mice that died during the first 2 days (usually around 20% in all groups) were considered as treatment casualties and thus are not presented; each group contained 4-7 mice that survived after day 2.
*Indicates significant decrease in macroscopic manifestation in GA-treated versus untreated mice ($p < 0.05$).

TABLE 3

The effect of various courses of GA treatment on the macroscopic manifestations of TNBS-induced colitis in different mouse strains

| | | | Macroscopic scoring of colon damage | | | | |
|---|---|---|---|---|---|---|---|
| Mouse Strain | Treatment | N | Ulceration (max 10) | Adhesion (max 2) | Diarrhea (max 1) | Thickness (max 1) | Total Score (max 14) |
| SJL/JxBALB/c (scoring 5 days after disease induction) | Control | 8 | 6.8 | 1.6 | 0.7 | 0.5 | 9.6 |
|  | GA oral every other day (from day −7) | 8 | 3.8 | 1.0 | 0.3 | 0.3 | 5.4 |
|  | GA injected once day −14 | 8 | 4.4 | 1.4 | 0.3 | 0.3 | 6.4 |
|  | GA injected daily (from day −7) | 7 | 1.4 | 0.8 | 0.4 | 0.1 | 2.7* |
|  | GA injected daily (from day −14) | 7 | 1.4 | 0.4 | 0.2 | 0.1 | 2.1* |
| SJL/JxBALB/c (scoring 11 days after disease induction) | Control | 7 | 3.3 | 1.1 | 0.4 | 0.4 | 5.3 |
|  | GA oral every other day (from day −7) | 7 | 2.3 | 0.6 | 0.1 | 0.2 | 3.2 |
|  | GA injected once day −14 | 6 | 2.3 | 1.0 | 0.2 | 0.2 | 3.7 |
|  | GA injected daily (from day −7) | 8 | 0.1 | 0.0 | 0.0 | 0.0 | 0.1* |
|  | GA injected daily (from day −14) | 8 | 0.1 | 0.0 | 0.0 | 0.0 | 0.1* |
| SJL/J (scoring 5 days after disease induction) | Control | 10 | 8.4 | 2.0 | 1.0 | 1.0 | 12.5 |
|  | GA oral every other day (from day −7) | 11 | 7.1 | 1.8 | 0.9 | 0.9 | 10.7 |
|  | GA injected daily (from day −7) | 11 | 3.5 | 1.2 | 0.5 | 0.5 | 5.7* |

Colitis was induced by TNBS in 50% ethanol. GA was administered by one of the following ways: orally (0.25 mg), 8 feedings starting 7 days before disease induction; by one injection (5 mg/mouse) SC in ICFA, 14 days before disease induction; by daily injections (2.5 mg/mouse) SC starting either 14 or 7 days before disease induction. Mice that died during the first 2 days (usually around 20% in all groups) were considered as treatment casualties and are not presented.
*Indicates significant decrease in macroscopic manifestation in GA-treated versus untreated mice ($p < 0.05$).

REFERENCES

Aharoni R, Teitelbaum D, Sela M, et al. Copolymer 1 induces T cells of the T helper type 2 that crossreact with myelin basic protein and suppress experimental autoimmune encephalomyelitis. *Proc. Natl. Acad. Sci. USA.* 94:10821-6 (1997)

Aharoni R, Teitelbaum D, Sela M, Arnon R. Bystander suppression of experimental autoimmune encephalomyelitis by T cell lines and clones of the Th2 type induced by Copolymer 1. *J. Neuroimmunol.* 91:135-46 (1998)

Aharoni R., Teitelbaum D., Arnon R., Sela M. Copolymer 1 inhibits manifestations of graft rejection. *Transplantation* 27: 598-605 (2001)

Bregenholt S. Cells and cytokines in the pathogenesis of inflammatory bowel disease: new insights from mouse T-cell transfer models. *Exp Clin Immunogenet* 17: 115-29 (2000)

Elson C O, Beagley K W, Shannanov A T, Fujihashi K, Kiyono H, Tennyson G S, Cong Y, Black C A, Ridwan B W, McGhee J R. Hapten-induced model of murine inflammatory bowel disease mucosa immune responses and protection by tolerance. *J Immunol* 157:2174-2185 (1996)

Fridkis-Hareli M, Teitelbaum D, Gurevich E, et al. Direct binding of myelin basic protein and synthetic copolymer 1 to class II major histocompatibility complex molecules on living antigen-presenting cells—specificity and promiscuity. *Proc. Natl. Acad. Sci. USA.* 91:4872-6 (1994)

Fridkis-Hareli M, Neveu J M, Robinson R A, Lane W S, Gauthier L, Wucherpfennig K W, Sela M, Strominger J L. Binding motifs of copolymer 1 to multiple sclerosis- and rheumatoid arthritis-associated HLA-DR molecules. *J Immunol.* 162:4697-4704 (1999)

Fridkis-Hareli M, Santambrogio L, Stem J N, Fugger L, Brosnan C, Strominger J L. Novel synthetic amino acid copolymers that inhibit autoantigen-specific T cell responses and suppress experimental autoimmune encephalomyelitis. *J Clin Invest* 109:1635-1643 (2002)

Johnson K P, B R Brooks, J A Cohen, C C Ford, J Goldstein, R P Lisak, L W Myers, H S Panitch, J W Rose, and R B Schiffer. Copolymer 1 reduces relapse rate and improves disability in relapsing-remitting multiple sclerosis: results of a phase III multicenter, double-blind placebo-controlled trial. The Copolymer 1 Multiple Sclerosis Study Group. *Neurology* 45:1268-1276 (1995)

Kipnis, J. and Schwartz, M. Dual Action of Glatiramer Acetate (Cop-1) as a Treatment for Autoimmune Diseases and a Vaccine for Protective Autoimmunity after CNS Injury. *Trends Mol. Med.* 8: 319-323 (2002)

MacDonald T T, Monteleone G, Pender S L F Recent developments in the immunology of inflammatory bowel disease. *Scand. J. Immunol.* 51:2-9 (2000)

Neuhaus O, Farina C, Yassouridis A, Wiendl H, Then Bergh F, Dose T, Wekerle H, Hohlfeld R. Multiple sclerosis: comparison of Copolymer-1 reactive T cell lines from treated and untreated subjects reveals cytokine shift from T helper T helper 2 cells. *Proc. Natl. Acad. Sci. USA.* 97:7452-7 (2000)

Reuter B K, Asfaha S, Buret A, Sharkey K A, Wallace J L. Exacerbation of inflammation-associated colonic injury in rat through inhibition of cyclooxygenase-2. *J. Clin. Invest.* 98:2076-85 (1996)

Sandborn W J, Targan S R Biologic therapy of inflammatory bowel disease. *Gastroenterol.* 122: 1592-608 (2002)

Schlegel P G, Aharoni R, Chen Y, Chen J, Teitelbaum D, Arnon R, Sela M, Chao N J. A synthetic random copolymer with promiscuous binding to class II MHC molecules inhibits T-cell proliferative response to major and minor histocompatibility antigens in vitro and confers the capacity to prevent murine graft-versus-host disease in vivo. *Proc. Natl. Acad. Sci. USA.* 93: 5061-6 (1996)

Sela M, Teitelbaum D. Glatiramer acetate in the treatment of multiple sclerosis. *Expert Opin. Pharmacother.* 2:1149-65 (2001)

Shanahan F. Inflammatory bowel disease: Immunodiagnostics, immunotherapeutics, and ectotherapeutics. *Gastroenterol.* 120: 622-35 (2001)

Van Deventer S J H Immunotherapy of Crohn's disease. *Scand. J. Immunol.* 51: 18-22 (2000)

Wirtz S., Neurath M. Animal models of intestinal inflammation: new insights into the molecular pathogenesis and immunotherapy of inflammatory bowel disease. *Int J. Colorectal Dis* 15:144-160 (2000)

The invention claimed is:

1. A method for inhibiting weight loss, inducing weight regain or reducing macroscopic colonic damage in a patient suffering from severe Crohn's disease, comprising administering to said patient by daily injection an amount of an active agent selected from the group consisting of
   i) Copolymer 1 and Copolymer 1-related peptides consisting of random three- or four-amino acid copolymers made up of one amino acid selected from three or four of the following groups:
      (a) lysine and arginine;
      (b) glutamic acid and aspartic acid;
      (c) alanine and glycine; and
      (d) tyrosine and tryptophan; and
   ii) a Copolymer 1-related peptide having the sequence of any of SEQ ID NOs: 1-32,
in an amount effective for inhibiting weight loss, inducing weight regain or reducing macroscopic colonic damage in the patient.

2. The method of claim 1, wherein said active agent is Copolymer 1-related peptide consisting of random three- or four-amino acid copolymers made up of one amino acid selected from three or four of the following groups:
   (a) lysine and arginine;
   (b) glutamic acid and aspartic acid;
   (c) alanine and glycine; and
   (d) tyrosine and tryptophan.

3. The method of claim 1 wherein the active agent is administered to a patient suffering from severe Crohn's disease in an amount effective to inhibit weight loss.

4. The method of claim 3 wherein the daily injection is daily subcutaneous injection.

5. The method of claim 4 wherein the active agent is Copolymer 1.

6. The method of claim 1 wherein the active agent is administered to a patient suffering from severe Crohn's disease in an amount effective to induce weight regain.

7. The method of claim 6 wherein the daily injection is daily subcutaneous injection.

8. The method of claim 7 wherein the active agent is Copolymer 1.

9. The method of claim 1 wherein the active agent is administered to a patient suffering from severe Crohn's disease in an amount effective to reduce macroscopic colonic damage.

10. The method of claim 9 wherein the macroscopic colonic damage is determined by a macroscopic parameter selected from the group consisting of
    (a) degree of colonic ulceration;
    (b) degree of intestinal and peritoneal adhesion;
    (c) diarrhea; and
    (d) degree of bowel wall thickness.

11. The method of claim 9 wherein the macroscopic colonic damage is determined by the degree of colonic ulceration and the degree of colonic ulceration is reduced.

12. The method of claim 11 wherein the daily injection is subcutaneous injection.

13. The method of claim 12 wherein the active agent is Copolymer 1.

14. The method of claim 9 wherein the macroscopic colonic damage is determined by the degree of intestinal and peritoneal adhesion and the degree of intestinal and peritoneal adhesion is reduced.

15. The method of claim 14 wherein the degree of intestinal and peritoneal adhesion is reduced the daily injection is daily subcutaneous injection.

16. The method of claim 15 wherein the active agent is Copolymer 1.

17. The method of claim 9 wherein the macroscopic colonic damage is determined by the level of diarrhea and the level of diarrhea is reduced.

18. The method of claim 17 wherein the daily injection is daily subcutaneous injection.

19. The method of claim 18 wherein the active agent is Copolymer 1.

20. The method of claim 9 wherein the macroscopic colonic damage is determined by the degree of bowel wall thickness and bowel wall thickening is inhibited.

21. The method of claim 20 wherein the daily injection is daily subcutaneous injection.

22. The method of claim 21 wherein the active agent is Copolymer 1.

* * * * *

SEQUENCE LISTING

```
<160> NUMBER OF SEQ ID NOS: 32

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Ala Ala Ala Tyr Ala Ala Ala Ala Ala Ala Lys Ala Ala Ala Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2
```

```
Ala Glu Lys Tyr Ala Ala Ala Ala Ala Lys Ala Ala Ala Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide

<400> SEQUENCE: 3

Ala Lys Glu Tyr Ala Ala Ala Ala Ala Lys Ala Ala Ala Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide

<400> SEQUENCE: 4

Ala Lys Lys Tyr Ala Ala Ala Ala Ala Lys Ala Ala Ala Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide

<400> SEQUENCE: 5

Ala Glu Ala Tyr Ala Ala Ala Ala Ala Lys Ala Ala Ala Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Lys Glu Ala Tyr Ala Ala Ala Ala Ala Lys Ala Ala Ala Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Ala Glu Glu Tyr Ala Ala Ala Ala Ala Lys Ala Ala Ala Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

Ala Ala Glu Tyr Ala Ala Ala Ala Ala Ala Lys Ala Ala Ala Ala
1               5                   10                  15
```

```
<210> SEQ ID NO 9
<211> LENGTH: 15
<212> TYPE: PRT
<213> ORGANISM: Artificial Sequence
<220> FEATURE:
<223> OTHER INFORMATION: Synthetic peptide

<400> SEQUENCE: 9

Glu Lys Ala Tyr Ala Ala Ala Ala Ala Lys Ala Ala Ala Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Ala Ala Lys Tyr Glu Ala Ala Ala Ala Lys Ala Ala Ala Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Ala Ala Lys Tyr Ala Glu Ala Ala Ala Lys Ala Ala Ala Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Glu Ala Ala Tyr Ala Ala Ala Ala Ala Lys Ala Ala Ala Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide

<400> SEQUENCE: 13

Glu Lys Lys Tyr Ala Ala Ala Ala Ala Lys Ala Ala Ala Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide

<400> SEQUENCE: 14

Glu Ala Lys Tyr Ala Ala Ala Ala Ala Lys Ala Ala Ala Ala
1               5                   10                  15
```

```
<210> SEQ ID NO 15
<211> LENGTH: 15
<212> TYPE: PRT
<213> ORGANISM: Artificial Sequence
<220> FEATURE:
<223> OTHER INFORMATION: Synthetic peptide

<400> SEQUENCE: 15

Ala Glu Lys Tyr Ala Ala Ala Ala Ala Ala Ala Ala Ala Ala Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Ala Lys Glu Tyr Ala Ala Ala Ala Ala Ala Ala Ala Ala Ala Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide

<400> SEQUENCE: 17

Ala Lys Lys Tyr Glu Ala Ala Ala Ala Ala Ala Ala Ala Ala Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide

<400> SEQUENCE: 18

Ala Lys Lys Tyr Ala Glu Ala Ala Ala Ala Ala Ala Ala Ala Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Ala Glu Ala Tyr Lys Ala Ala Ala Ala Ala Ala Ala Ala Ala Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide

<400> SEQUENCE: 20

Lys Glu Ala Tyr Ala Ala Ala Ala Ala Ala Ala Ala Ala Ala Ala
1               5                   10                  15

<210> SEQ ID NO 21
<211> LENGTH: 15
```

```
<212> TYPE: PRT
<213> ORGANISM: Artificial Sequence
<220> FEATURE:
<223> OTHER INFORMATION: Synthetic peptide

<400> SEQUENCE: 21

Ala Glu Glu Tyr Lys Ala Ala Ala Ala Ala Ala Ala Ala Ala Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide

<400> SEQUENCE: 22

Ala Ala Glu Tyr Lys Ala Ala Ala Ala Ala Ala Ala Ala Ala Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Glu Lys Ala Tyr Ala Ala Ala Ala Ala Ala Ala Ala Ala Ala Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

Ala Ala Lys Tyr Glu Ala Ala Ala Ala Ala Ala Ala Ala Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Ala Ala Lys Tyr Ala Glu Ala Ala Ala Ala Ala Ala Ala Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide

<400> SEQUENCE: 26

Glu Lys Lys Tyr Ala Ala Ala Ala Ala Ala Ala Ala Ala Ala Ala
1               5                   10                  15

<210> SEQ ID NO 27
<211> LENGTH: 15
<212> TYPE: PRT
<213> ORGANISM: Artificial Sequence
```

```
<220> FEATURE:
<223> OTHER INFORMATION: Synthetic peptide

<400> SEQUENCE: 27

Glu Ala Lys Tyr Ala Ala Ala Ala Ala Ala Ala Ala Ala Ala Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide

<400> SEQUENCE: 28

Ala Glu Tyr Ala Lys Ala Ala Ala Ala Ala Ala Ala Ala Ala Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic peptide

<400> SEQUENCE: 29

Ala Glu Lys Ala Tyr Ala Ala Ala Ala Ala Ala Ala Ala Ala Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic peptide

<400> SEQUENCE: 30

Glu Lys Tyr Ala Ala Ala Ala Ala Ala Ala Ala Ala Ala Ala Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic peptide

<400> SEQUENCE: 31

Ala Tyr Lys Ala Glu Ala Ala Ala Ala Ala Ala Ala Ala Ala Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic peptide

<400> SEQUENCE: 32

Ala Lys Tyr Ala Glu Ala Ala Ala Ala Ala Ala Ala Ala Ala Ala
1               5                   10                  15
```